United States Patent [19]
Klein et al.

[11] Patent Number: 5,417,699
[45] Date of Patent: May 23, 1995

[54] DEVICE AND METHOD FOR THE PERCUTANEOUS SUTURING OF A VASCULAR PUNCTURE SITE

[75] Inventors: Enrique J. Klein, Los Altos; T. Daniel Gross, Los Gatos; Tomoaki Hinohara, Portola Valley; James W. Vetter, Redwood City, all of Calif.

[73] Assignee: Perclose Incorporated, Sunnyvale, Calif.

[21] Appl. No.: 989,611

[22] Filed: Dec. 10, 1992

[51] Int. Cl.⁶ .............................................. A61B 17/00
[52] U.S. Cl. .................................. 606/144; 606/139; 606/223; 112/80.03; 112/169; 604/900
[58] Field of Search .............. 606/139, 144, 145, 147, 606/148, 157, 158, 184, 187, 222, 223; 112/169, 80.03; 604/168, 900

[56] References Cited

U.S. PATENT DOCUMENTS

| | | | |
|---|---|---|---|
| 312,408 | 2/1885 | Wackerhagen | 606/223 |
| 659,422 | 10/1900 | Shidler . | |
| 2,646,045 | 7/1953 | Priestley . | |
| 2,959,172 | 11/1960 | Held . | |
| 3,665,926 | 5/1972 | Flores . | |
| 3,939,820 | 2/1976 | Grayzel . | |
| 4,161,951 | 7/1979 | Scanlan, Jr. | 606/145 |
| 4,317,445 | 3/1982 | Robinson | 604/168 |
| 4,493,323 | 1/1985 | Albright et al. | 606/139 |
| 4,587,969 | 5/1986 | Gillis . | |
| 4,744,364 | 5/1988 | Kensey . | |
| 4,852,568 | 8/1989 | Kensey . | |
| 4,890,612 | 1/1990 | Kensey . | |
| 4,929,246 | 5/1990 | Sinofsky . | |
| 5,021,059 | 6/1991 | Kensey et al. . | |
| 5,047,039 | 10/1991 | Avant et al. | 606/148 |
| 5,061,274 | 10/1991 | Kensey . | |
| 5,160,339 | 11/1992 | Chen et al. | 606/157 |
| 5,171,251 | 12/1992 | Bregen et al. | 606/157 |
| 5,192,302 | 3/1993 | Kensey et al. | 606/213 |
| 5,222,974 | 6/1993 | Kensey et al. | 606/213 |
| 5,304,184 | 4/1994 | Hathaway | 606/148 |
| 5,320,632 | 6/1994 | Heidmueller | 606/144 |

FOREIGN PATENT DOCUMENTS

| | | |
|---|---|---|
| 0140557 | 5/1985 | European Pat. Off. . |
| 4210724 | 7/1983 | Germany . |
| 1093329 | 5/1984 | U.S.S.R. . |
| 1174036 | 8/1985 | U.S.S.R. . |

OTHER PUBLICATIONS

"Innovation Through Progress", Rema-Medizintechnik GbmH, Jan. 1992.
Datascope Corporation, Montvale, N.J., (1991) 1 page, American Heart Assoc. meeting, Anaheim.
Kensey Nash Corporation, Exton, Pa., "The Hemostatic Puncture Closure Device", 2 pages.

*Primary Examiner*—Stephen C. Pellegrino
*Assistant Examiner*—Jeffrey A. Schmidt
*Attorney, Agent, or Firm*—Townsend and Townsend Khourie and Crew

[57] ABSTRACT

A suture applying device comprises a shaft which carries a pair of needles near its distal end. The needles are joined by a length of suture, and the shaft is used to both introduce the needles into a lumen of a body structure and to push the needles back through tissue on either side of the puncture site. After the needles have passed through the tissue, they are captured on the shaft and drawn outward through the tract, leaving a loop of suture behind to close the puncture site near the body lumen. The suture can then be tied and the knot pushed back through the tract to complete the closure. Alternatively, a locking fastener formed of a resorbable material can be placed into the penetration over the sutures and the sutures tied over the fastener.

43 Claims, 21 Drawing Sheets

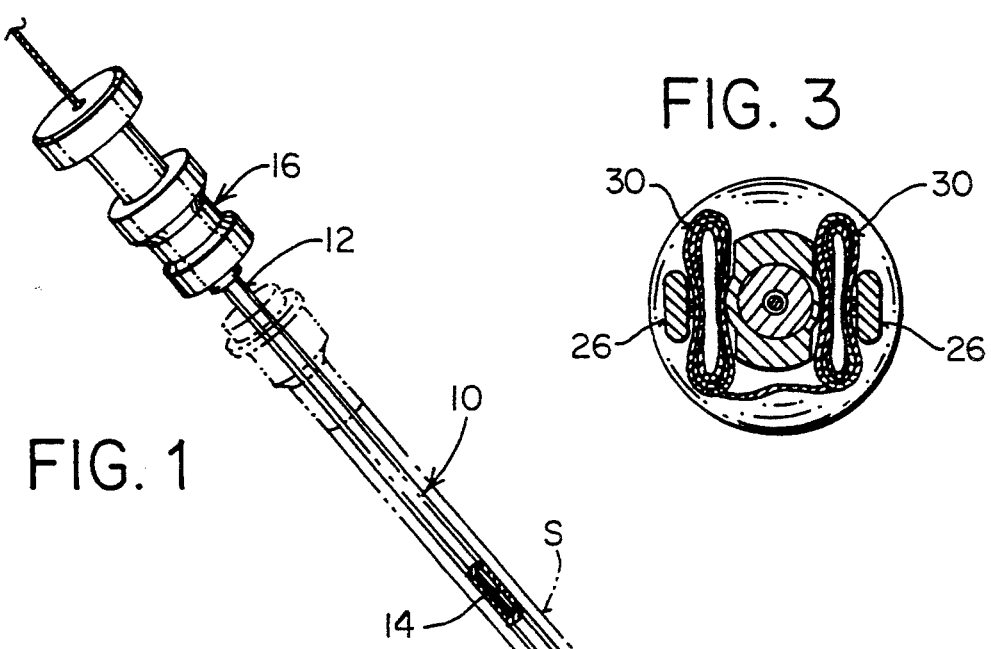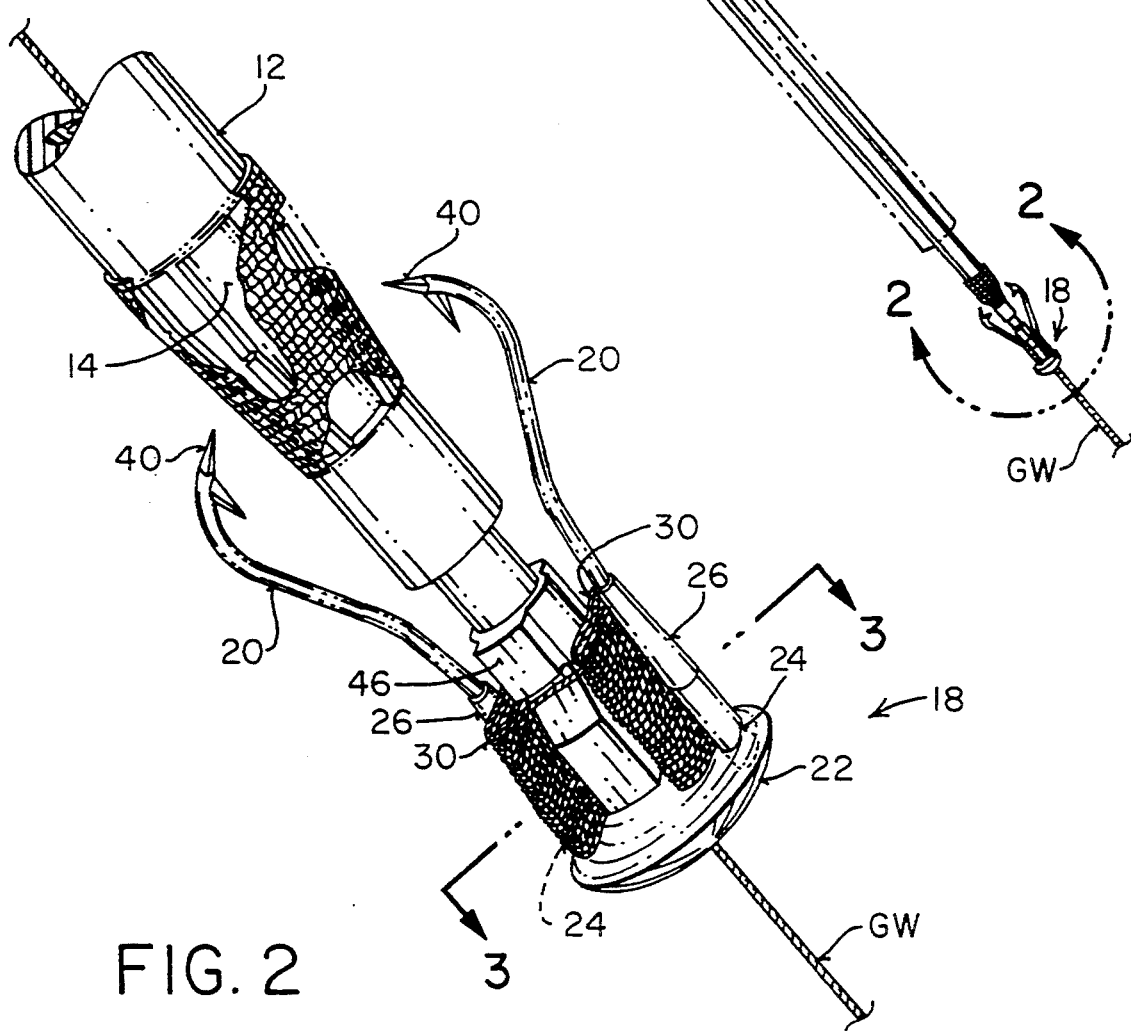

FIG. 7
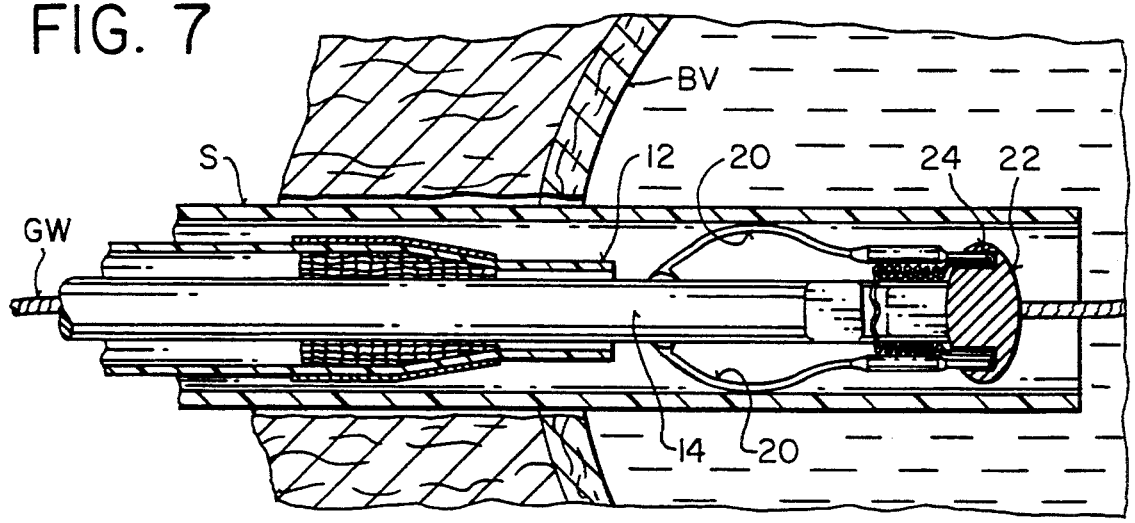
FIG. 8
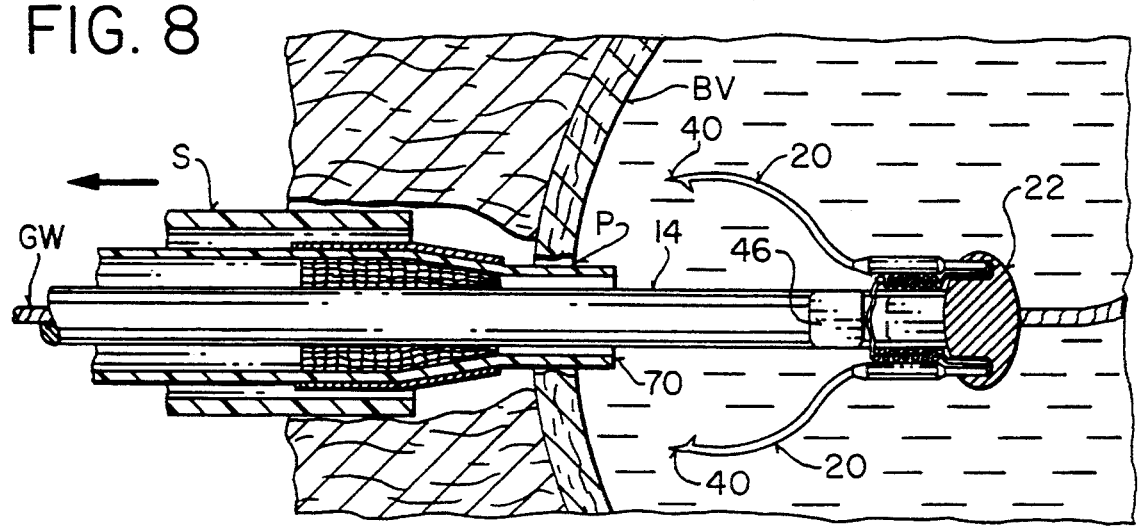
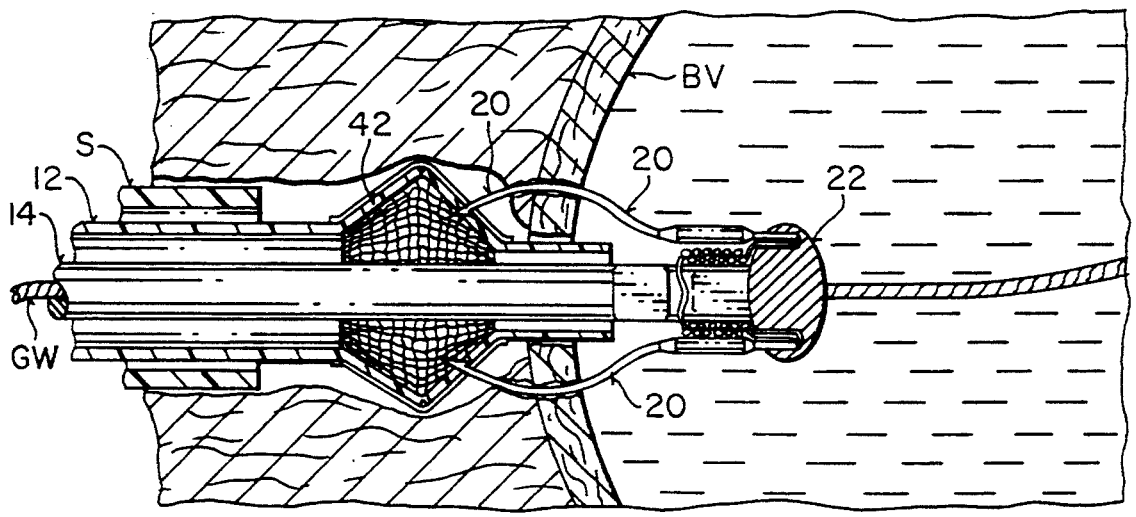
FIG. 9

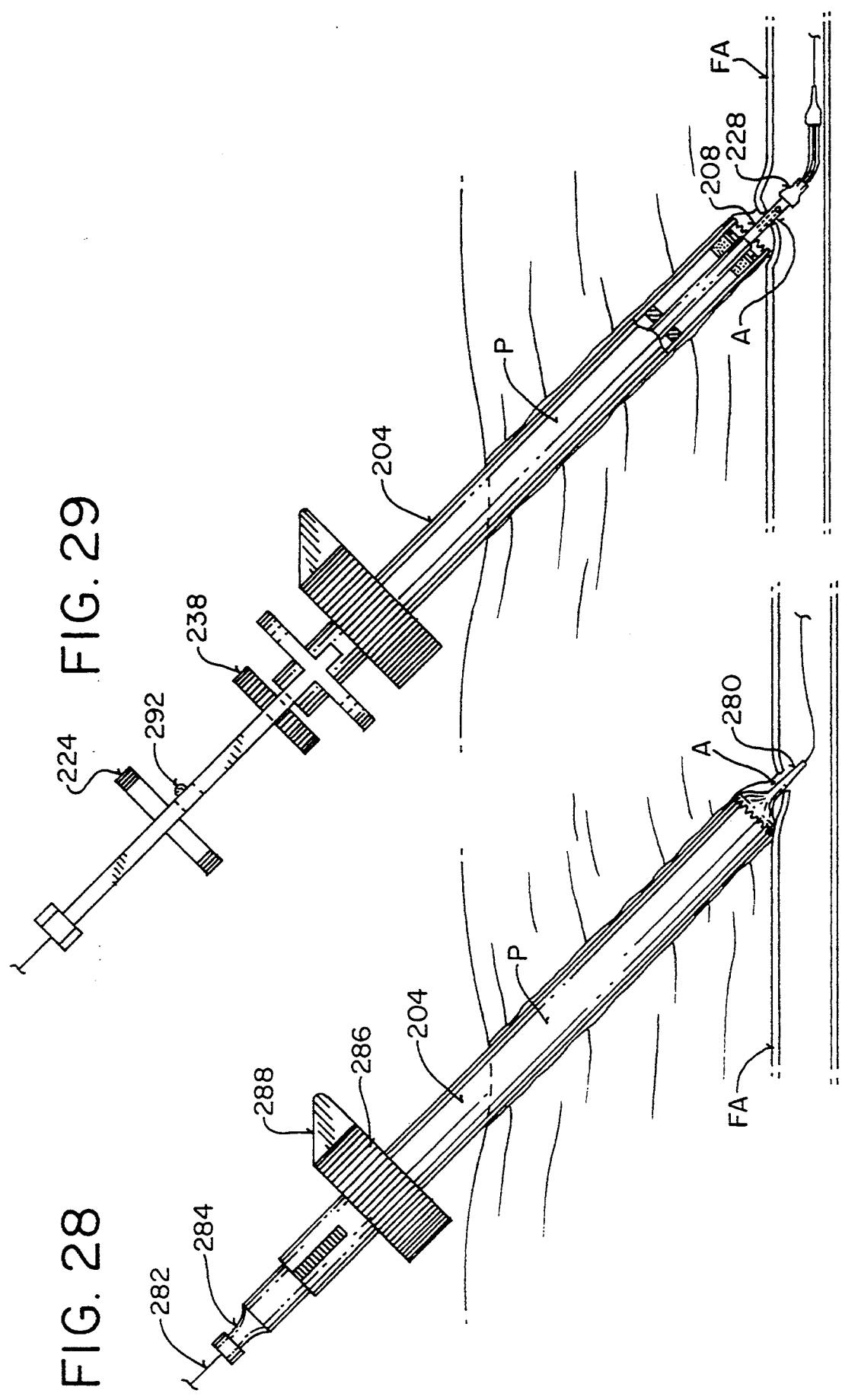

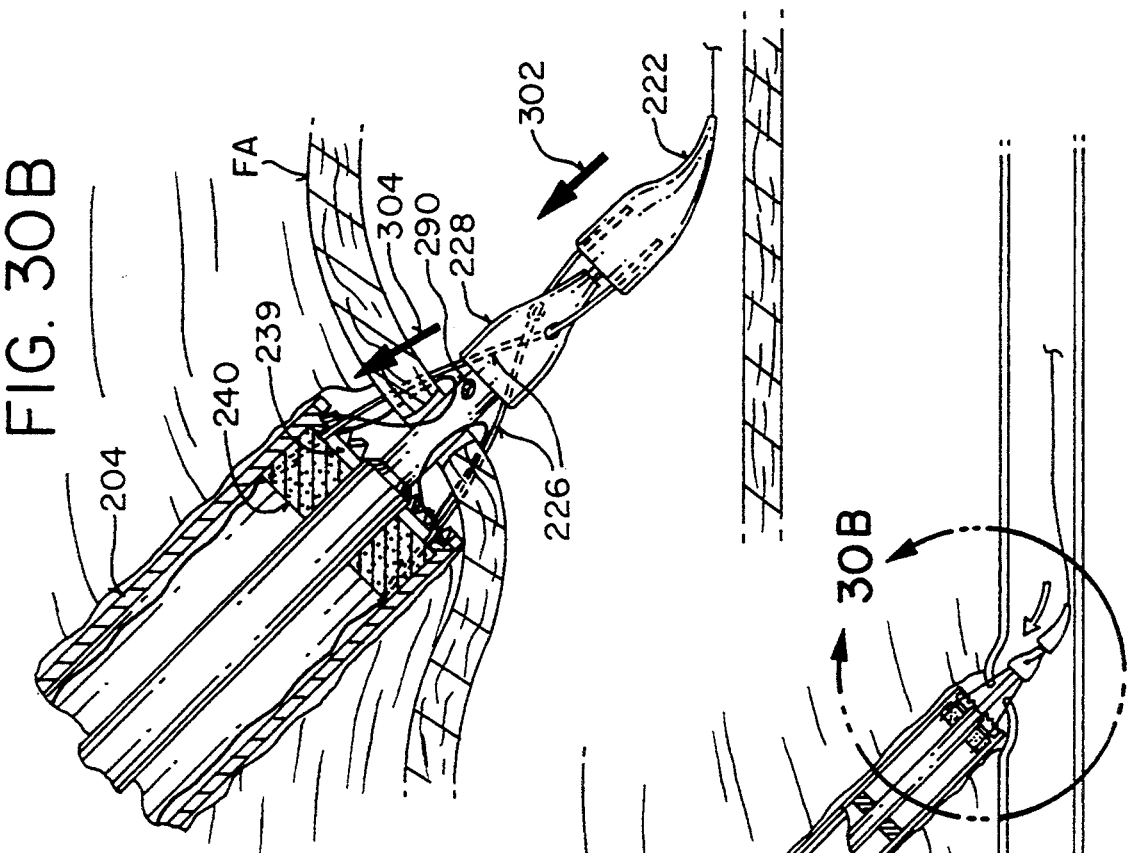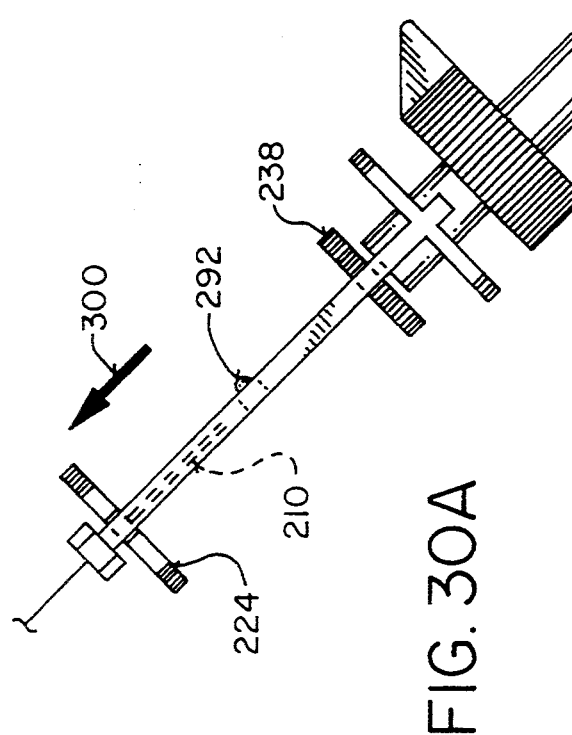

DEVICE AND METHOD FOR THE PERCUTANEOUS SUTURING OF A VASCULAR PUNCTURE SITE

BACKGROUND OF THE INVENTION

1. Field of the Invention

The present invention relates generally to devices and methods for the percutaneous closure of body lumens. More particularly, the present invention relates to devices and methods for the percutaneous closure of arterial and venous puncture sites, which are usually accessible only through a tissue tract.

A number of diagnostic and interventional vascular procedures are now performed transluminally, where a catheter is introduced to the vascular system at a convenient access location and guided through the vascular system to a target location using established techniques. Such procedures require vascular access which is usually established using the well known Seldinger technique, as described, for example, in William Grossman's "Cardiac Catheterization and Angiography," 3rd Ed., Lea and Febiger, Philadelphia, 1986, incorporated herein by reference.

When vascular access is no longer required, the introducer sheath must be removed and bleeding at the puncture site stopped. One common approach to attempt providing hemostasis (the cessation of bleeding) is to apply external force near and upstream from the puncture site, typically by manual or "digital" compression. This approach suffers from a number of disadvantages. It is time-consuming, frequently requiring one-half hour or more of compression before hemostasis is assured. This procedure is uncomfortable for the patient and frequently requires administering analgesics to be tolerable. Moreover, the application of excessive pressure can at times totally occlude the underlying blood vessel, resulting in ischemia and/or thrombosis. Following manual compression the patient is required to remain recumbent for at least six and at times as long as eighteen hours under close observation to assure continued hemostasis. During this time renewed bleeding may occur resulting in bleeding through the tract, hematoma and/or pseudoaneurism formation as well as arteriovenous fistula formation. These complications may require blood transfusion and/or surgical intervention. The incidence of these complications increases when the sheath size is increased and when the patient is anticoagulated. It is clear that the standard technique for arterial closure can be risky, and is expensive and onerous to the patient. While the risk of such conditions can be reduced by using highly trained individuals, such use is both expensive and inefficient.

To overcome the problems associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolize downstream causing vascular occlusion. Also, thrombus formation on the surface of a fastener protruding into the lumen can cause a stenosis which can obstruct normal blood flow. Other possible complications include infection as well as adverse reactions to the collagen implant.

For these reasons, it would be desirable to provide improved devices and methods to seal body lumen puncture sites. It would be particularly desirable to provide percutaneous devices and methods for suturing the puncture sites required for percutaneous vascular procedures.

2. Description of the Background Art

Devices capable of delivering pairs of needles to various tissue locations are described in the following patents and patent applications: U.S. Pat. Nos. 4,493,323 and 659,422; European patent application 140 557; and U.S.S.R patent applications 1174-036-A and 1093-329-A. Other suturing and ligating devices are described in U.S. Pat. Nos. 3,665,926; 2,959,172; and 2,646,045. Devices for sealing percutaneous vascular penetrations using various fastener structures are described in U.S. Pat. Nos. 5,061,274; 5,021,059; 4,929,246; 4,890,612; 4,852,568; 4,744,364; 4,587,969; and 3,939,820. Collagen fastener sealing devices are under commercial development by Datascope Corp., Montvale, N.J., and Kensey Nash Corporation, Exton, Pa.

SUMMARY OF THE INVENTION

The present invention provides devices and methods for suturing percutaneous lumenal puncture sites. The devices will comprise a shaft, a pair of needles removably carried near the distal end of the shaft, and a length of suture secured to and extending between the needles. As described below, the shaft is used to introduce the needles inwardly through the tract and puncture site and into the lumen. Thereafter, the shaft is used to draw the needles outwardly back through the tissue on either side of the puncture site to begin forming a loop of the suture at the intimal surface of the puncture site. The device may further include means on the shaft for capturing the pointed ends of the needles after they have passed through the tissue and back into the tract, and the shaft can then be withdrawn to carry the needles and attached suture outwardly back through the tract. Alternatively, the shaft and needles can be made sufficiently long so that the pointed ends of the needles may be drawn completely through the tract so that they may be manually grasped (without the need for capture on the shaft). In either case, the free ends of the suture can then be tied (or otherwise secured) and the resulting knot pushed back through the tract to complete the suture loop at the adventitial surface of the puncture site. The ability to provide a secured suture loop at the puncture site is particularly advantageous since a reliable closure is formed. Furthermore, suture closure of puncture sites has been universally accepted as the standard of care for many decades.

The devices and methods of the present invention are useful whenever it is desirable to place a tied suture loop to close a lumen puncture site, and will be particularly useful for suturing percutaneous vascular puncture sites. The devices can achieve closure wholly through the tract puncture site and can be manipulated entirely in a percutaneous manner. The present invention will find its greatest use in the sealing of femoral artery cannulation sites made in connection with percutaneous transluminal procedures, such as angiography, angioplasty, atherectomy, laser ablation, stent placement, intravascular imaging, and the like. The present invention will also find use in other medical procedures which rely on percutaneous access to hollow body organs and lumens, such as laparoscopic procedures, endoscopic procedures, artheroscopic procedures, and the like.

In a particular embodiment, the device of the present invention comprises the shaft, pair of needles, and length of suture, generally as described above. The device further comprises a sleeve received over the shaft and having a receiving area disposed near the distal end of the shaft. The device may also include means for expanding the receiving area and drawing the needles into the expanded receiving area, in order to capture the needles so that they may be withdrawn by the shaft through the tract. Conveniently, the expanding means may be an expandable cage and the receiving area may be defined by a fabric or mesh which will engage and entrap the needles (which are preferably barbed at their distal ends) so that they may be withdrawn by the shaft.

In a second particular aspect, the device of the present invention comprises a shaft, pair of needles, and length of suture, generally as described above, further in combination with a guide body having a proximal end, a distal end, and means for slidably receiving the flexible shaft therethrough, typically being a central lumen. The guide body further includes means at its distal end for retaining the pointed tips of the needles as the device is inserted through a percutaneous tract and puncture site and for guiding the needles in a desired pattern so that they will penetrate the arterial wall opposite each other around the puncture site. Preferably, the needles and portion of the shaft which extend beyond the distal end of the guide body are retained within a flexible sheath, with the suture being within or parallel to the sheath, which facilitates introduction of the device and helps align the needles as they are withdrawn by the shaft through the tissue. In this embodiment, the shaft and needles are sufficiently long so that the needles may be drawn outwardly through the tissue and entirely through the preexisting tract while still being held on the shaft. In this way, the pointed tips of the needles will be available so that the user can manually grasp and remove them. Securing of the suture will be accomplished as described above.

In a further aspect of the present invention, a fastener may be introduced over the free ends of the suture after they have been drawn outwardly through the percutaneous tract. The fastener is pushed into the tract to a location just superficial to the adventitial surface of the puncture site, and the fastener locked in place by rotating the fastener through at least one-half turn to cross over the two suture ends. The fastener may then be secured in place by tying the remaining free ends of the suture and pushing the resulting knot down onto the fastener.

The present invention still further provides a device for introducing the fastener just described. The fastener introducing device comprises a shaft having a proximal end and a distal end. Means at the distal end of the shaft are provided for detachably securing the fastener, and means of the proximal end of the shaft are provided for selectively detaching the fastener after it has been placed in the desired location within the percutaneous tract. The fastener includes at least two suture-receiving slots which permit the fastener to be introduced over the suture as it is introduced inwardly through the tract. After the fastener has been introduced sufficiently deep to be placed over the adventitial surface of the puncture site, the device may be used to turn the fastener prior to fastener detachment. The device is then removed and the free ends of the suture tied and the resulting knot pushed back down over the fastener to secure it in place.

BRIEF DESCRIPTION OF THE DRAWINGS

FIG. 1 is a perspective view of a suturing device constructed in accordance with the principles of the present invention.

FIG. 2 is a detailed view of the distal end of the suturing device of FIG. 1.

FIG. 3 is a cross-sectional view of the device of FIGS. 1 and 2, taken along line 3—3 of FIG. 2.

FIG. 7-12 illustrate use of the suturing device of FIG. 1 in applying and tying a suture loop through a percutaneous tract to a blood vessel wall.

FIG. 28 illustrates the introduction of the outer sheath which forms a part of the suturing device of FIG. 24A through a percutaneous tract.

FIG. 29 illustrates placement of the remaining portions of the suturing device within the sheath, as introduced in FIG. 28.

FIG. 30A illustrates initial needle penetration by drawing back the needle-carrying shaft of the suturing device introduced as in FIG. 29.

FIG. 30B is a detail view showing the needle penetration of FIG. 30A.

DESCRIPTION OF SPECIFIC EMBODIMENTS

Figure 4:
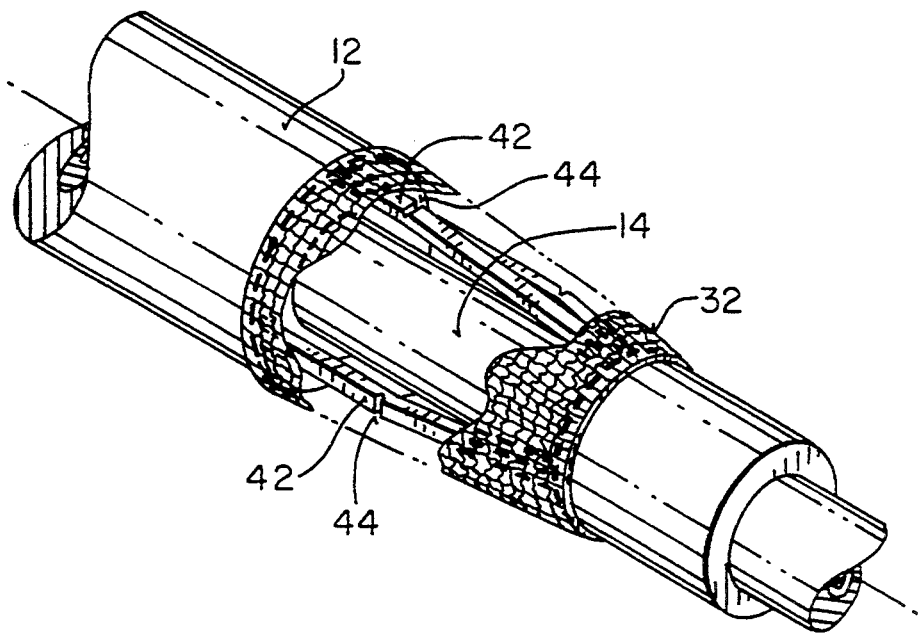
FIG. 4 is a detailed view of the distal end of the sleeve element of the device of FIG. 1, shown in its non-collapsed state.

Referring to FIGS. 1-3, a suture applying device 10 which is suitable for suturing and sealing of percutaneous vascular puncture site, particularly those made to the femoral artery in a patient's groin, will be described. It will be appreciated, however, that the device of the present invention can be readily adapted for use with punctures made to other hollow body organs and lumens, although it may be necessary to modify the dimensions and other particular aspects of the device to accommodate the different usage environment.

The device 10 of the present invention comprises an elongate body which includes an outer sleeve 12 and inner shaft 14. The shaft 14 is slidably positioned within the sleeve 12, with the sleeve and shaft being interconnected by a proximal actuator assembly 16 (best illustrated in FIG. 6). The inner shaft 14 will be hollow, defining a guidewire lumen (not illustrated) extending from the proximal actuator assembly 16 to the distal tip 18 of the device 10. In this way, the device 10 can be introduced over a conventional guidewire GW to facilitate introduction and manipulation of the device throughout the procedure, as described in detail hereinafter. The suture applying device 10 will be introduced through a conventional introducer sheath S, shown in phantom in FIG. 1. The ability to introduce the device 10 over the guidewire is not essential to the present invention, but will generally be preferred since most physicians desire that intravascular devices be manipulated over a guidewire. Introduction through the introducer sheath optionally provides containment of the suture as they are being introduced, as discussed hereinafter.

Referring in particular to FIGS. 2 and 3, suture needles 20 are carried in the suture retainer 22 which is mounted on the distal end of shaft 14. The suture retainer 22 includes a pair of slots 24 which serve as receptacles for the proximal shank portions 26 of each needle 20. The shank portions 26 will be shaped to mate with the slots 24 so that the needles 20 are maintained in a desired orientation. Preferably, the needles 20 include arcuate portions proximal to the tip which first extend radially outward from the shaft 14 but then turn back radially inward toward the shaft over their proximal-most portions. As described in greater detail hereinafter, this arcuate shape is desirable since it helps direct the needles 20 through a path in the tissue which brings them back into the shaft 14, where they can be captured by a capturing assembly which is described hereinafter.

Preferably, the needles will be composed of a highly resilient surgical metal, such as certain nickel titanium alloys, such as Nitinol ®. The use of such resilient alloys permits the needles to be compressed radially inward as the device 10 is introduced through the introducer sheath S. The needles 20 will spring back to their original shape, as illustrated in FIGS. 1 and 2, as soon as they pass from the distal end of the sheath S.

This ability to open or spread the needles 20 after they have been introduced through the introducer sheath S is important to the present invention since it is necessary to deploy the needles on either side of the percutaneous penetration. Such deployment of the needles could, of course, be achieved by a variety of mechanical mechanisms which would positively act on the needles to deflect them outwardly in the desired orientation. The use of inherently resilient springs, however, greatly simplifies the design of the device since no movable mechanical components are required to achieve the desired spreading of the needles 20.

The needle shanks 26 will typically be formed of stiffer material, such as stainless steel, to provide a strong base for retention within the needle retainer 22. Conveniently, the shanks may be formed from stainless steel hypodermic tubing which can be placed over and affixed to the butts of the needles 20 and flattened into a desired shape. The slots 24 can then be oriented to receive the flattened shanks 26 and hold the needles 20 in their preferred configuration as illustrated in FIG. 2.

The needles 20 are joined by a length of suture which is secured to the shank end 26 of each needle and extends therebetween. Conveniently, the suture 30 will be coiled between the shaft 14 and each needle shank 26, as best illustrated in FIG. 3. The suture should be stored on the device so that it is readily left behind in the body lumen as the device 10 is withdrawn through a percutaneous penetration, as described in greater detail hereinafter. To that end, it is desirable that the needle retainer 22 be smoothly shaped so that the suture can easily pass thereover as the device 10 is withdrawn.

Figure 5:
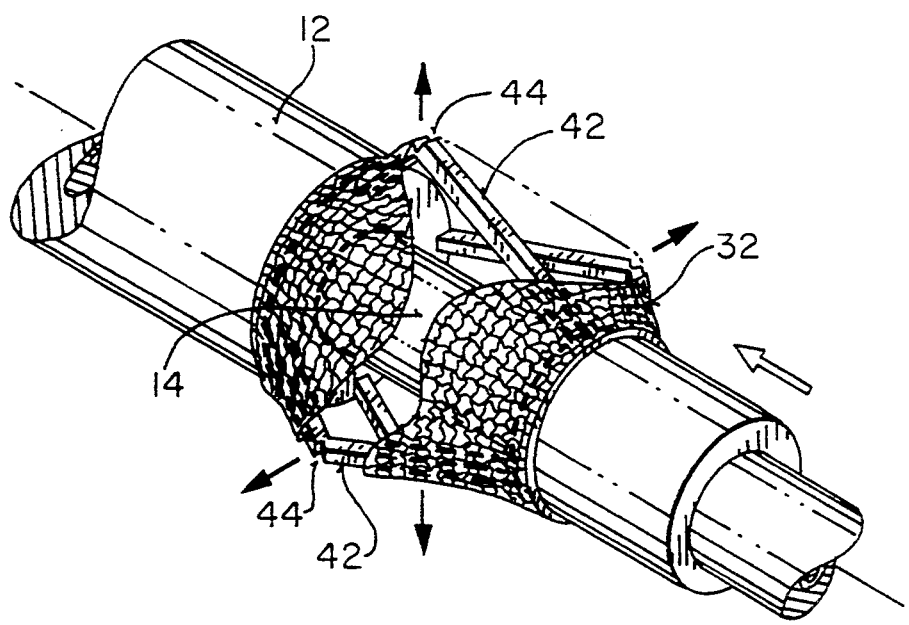
FIG. 5 is a view of the distal end of the sleeve element, similar to FIG. 4, shown in its collapsed configuration to define an enlarged receiving area.

Referring now also to FIGS. 4 and 5, the device 10 will carry a structure for capturing the needles 20 after they have been drawn through the tissue on either side of the percutaneous penetration. The structure may take a variety of forms, conveniently comprising a fabric or mesh surface 32 which defines an expandable receiving area for the needles. The needles 20 may include barbs 40 (FIG. 2) formed at or near their tips, and the barbs will be entrapped by the fabric or mesh surface 32 after they penetrate therethrough.

While it would be possible to provide a fixed receiving area, i.e. non-expandable, it will usually be preferable to provide a mechanism for expanding and orienting the receiving area to aid in capturing the needles 20. A variety of suitable expandable support structures could be provided, with the exemplary support structure being formed integrally as an expandable cage in the distal end of sleeve 12. The expandable cage includes a plurality of axial ribs 42 having hinged regions 44 so that the ribs may be expanded radially outward by compressing the sleeve 12 against a stop member 46 (mounted on the shaft 14 as best seen in FIG. 2), as will be described in more detail hereinafter.

In a preferred aspect of the present invention, the hinged regions 44 on axial ribs 42 of the cage structure on sleeve 12 will be unevenly axially spaced. By providing both symmetric hinge location, i.e. located in the middle of the rib, as well as asymmetric hinge location, the resulting asymmetric shape of the expandable cage will present a wider target of open windows for incoming needles 20. In this way, efficient capture of the barbed ends 40 of the needles 20 can be achieved.

Figure 6:
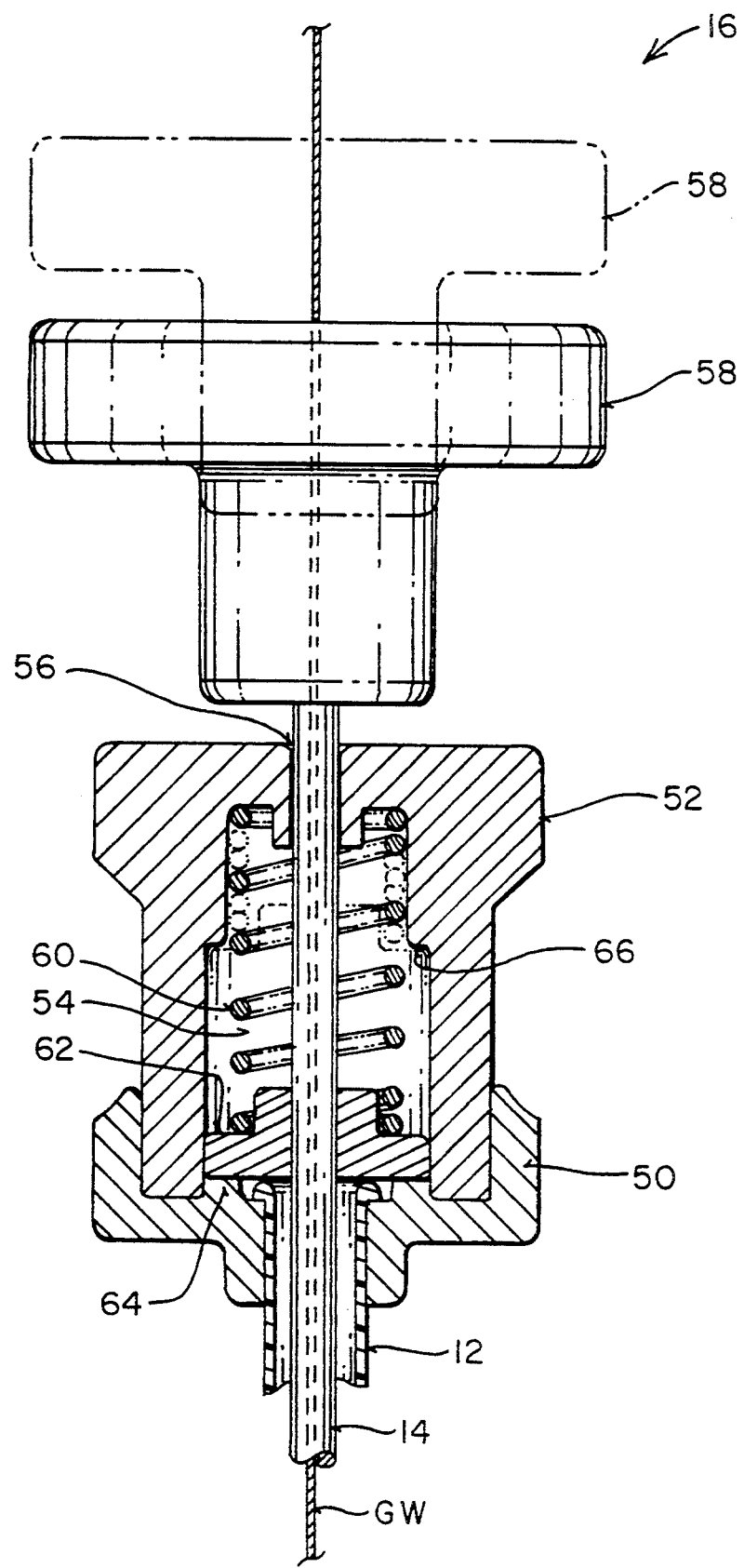
FIG. 6 is a cross-sectional view of the proximal end of the suturing device of FIG. 1.

Referring now in particular to FIG. 6, the proximal actuating assembly 16 includes a housing base 50 which is attached to the proximal end of sleeve 12 and a housing cap 52 which is secured to the housing base. The shaft 14 passes through an open interior 54 of the housing cap 52 and passes proximally outward through an aperture 56. A handle 58 is attached to the proximal end of the shaft 14 and permits a user to axially translate the shaft 14 relative to the sleeve 12. A compression spring 60 is mounted within the opening interior 54 of the housing cap 52 and acts against a piston element 62 which is fixedly secured to the shaft 14. The piston element 62 is located so that it lies against a distal travel stop 64 formed in the housing base 50 when the shaft 14 is disposed at the distal limit of its travel, as illustrated in FIG. 7.

The handle 58 can be used to draw the shaft 14 in the proximal axial direction until the piston element 62 engages an annular proximal travel stop 66 formed within the housing cap 52, as illustrated in broken line in FIG. 6. With the shaft 14 thus in its most proximal position, the cage structure will have been expanded and the needles 20 drawn into the receiving area, as illustrated in FIG. 9 and discussed in more detail hereinafter.

Referring now to FIGS. 7–12, use of the device 10 in applying and tying a suture loop in a blood vessel wall will be described in more detail. Referring in particular to FIG. 7, the device 10 is introduced through an introducer sheath S which may have been previously placed in connection with a conventional intravascular diagnostic or treatment protocol, such as angiography, angioplasty, atherectomy, laser ablation, cardiac mapping, cardiac ablation, or the like. The device 10 is introduced with the needles 20 compressed radially inward so that they will fit within the internal diameter of the sheath S. A particular advantage of the device 10 is that it can be introduced over the guidewire GW which has been used for performing the previous procedures. Thus, should it be necessary for any reason, the guidewire GW will remain in place until the very end of the suturing procedure.

As illustrated in FIG. 8, after the distal end of the device 10 including the needles 20 has reached the lumen of the blood vessel BV, the introducer sheath S will be partially withdrawn, permitting the resilient needles 20 to open radially outward so that the barbed tips 40 are disposed on opposite sides of the blood vessel wall tract P.

The user next draws proximally on the handle 58, causing the shaft 14 to move proximally relative to the sleeve 12. Proximal motion of the shaft 14, in turn, causes the needles 20 to penetrate through the blood vessel wall BV, with the arcuate shape of the needles causing the needles to move radially inward back toward the shaft 14. Continued proximal travel of the shaft 14 causes the stop member 46 to engage the distal end 70 of the sleeve member 12. Continued proximal travel of the shaft 14 thus causes axial compression of the sleeve 12, expanding individual ribs 42, as described above. The relative positions of the ribs 42 and needles 20 are chosen so that the expandable cage opens into the needles' path as they are brought backward through the blood vessel wall BV and surrounding tissue. The barbed ends 40 of the needles 20 are thus able to penetrate the fabric or mesh 32 carried on the expandable cage to engage and secure the needles. The situation where the needles have been secured is illustrated in FIG. 9.

Figure 10:
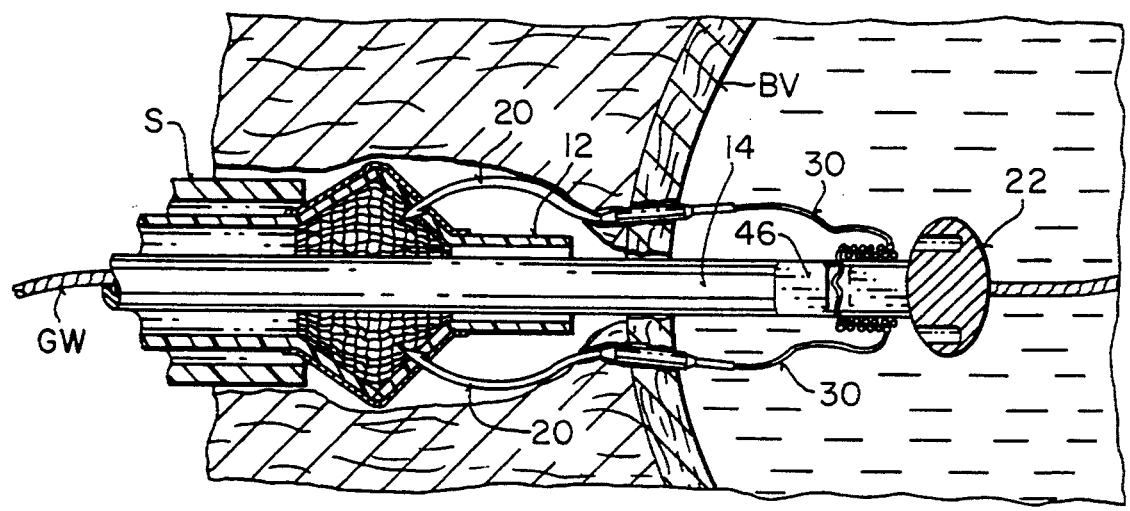

After the needles 20 are captured, the handle 58 is released, causing the shaft 14 to distally advance under the urging compression spring 60. Such distal motion of the shaft 14 causes the needle retainer 22 to move away from the needles 20 which are held by the fabric or mesh 32 on the expandable cage structure, as illustrated in FIG. 10.

Figure 11:
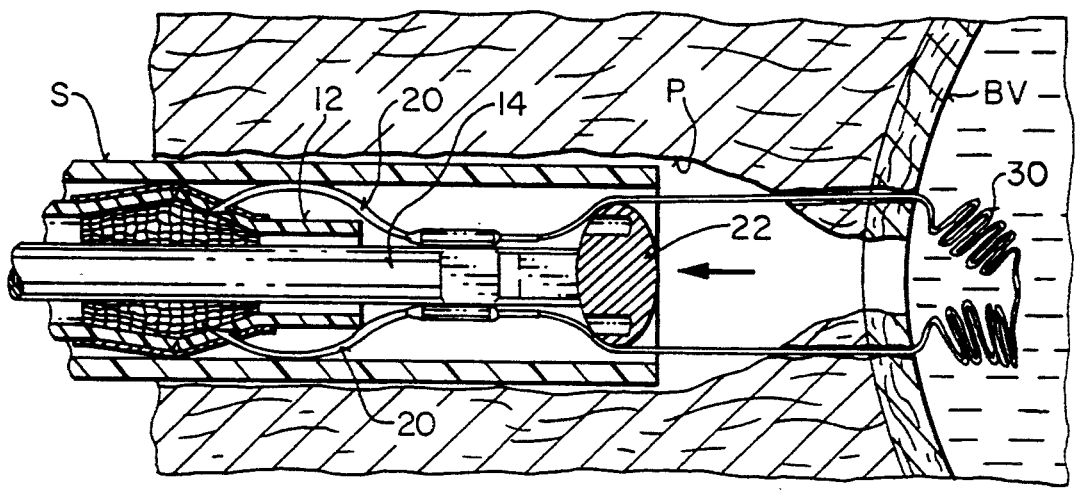

The device 10 may be drawn outward through the introducer sheath S, leaving the suture 30 behind (passing through the two needle penetrations made in the blood vessel wall BV and overlying tissue). The free ends of the suture 30 will thus be drawn outward through the percutaneous tract P, as illustrated in FIG. 11.)

Figure 12:
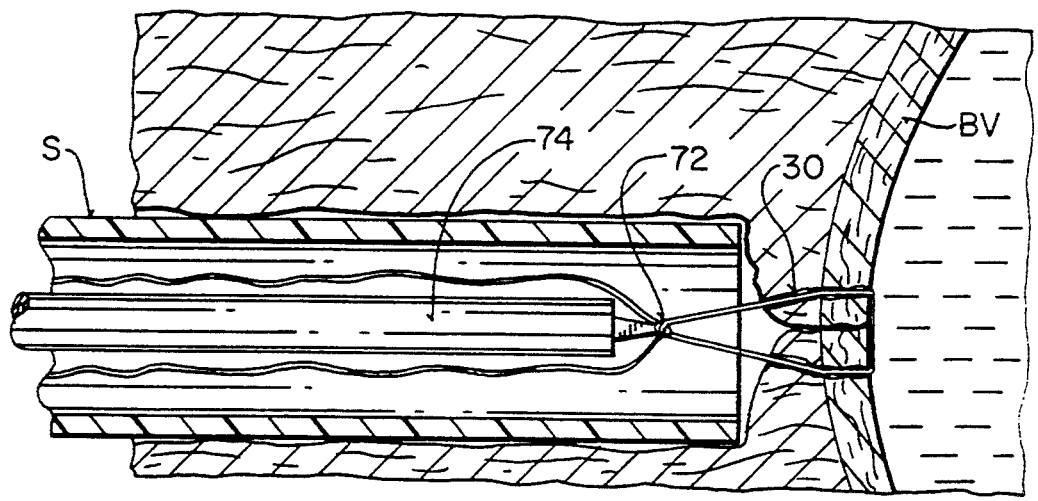

At this point, it will be possible to secure the free ends of the suture together, e.g., by tying to form a knot 72 which can be pushed downward using a pusher rod 74, as illustrated in FIG. 12. The introducer sheath may be removed either before or after the knot 72 is put in place. As an alternative to tying, various fasteners can be used to secure the free ends of the suture together, either alone or in combination with knotting.

Figure 13:
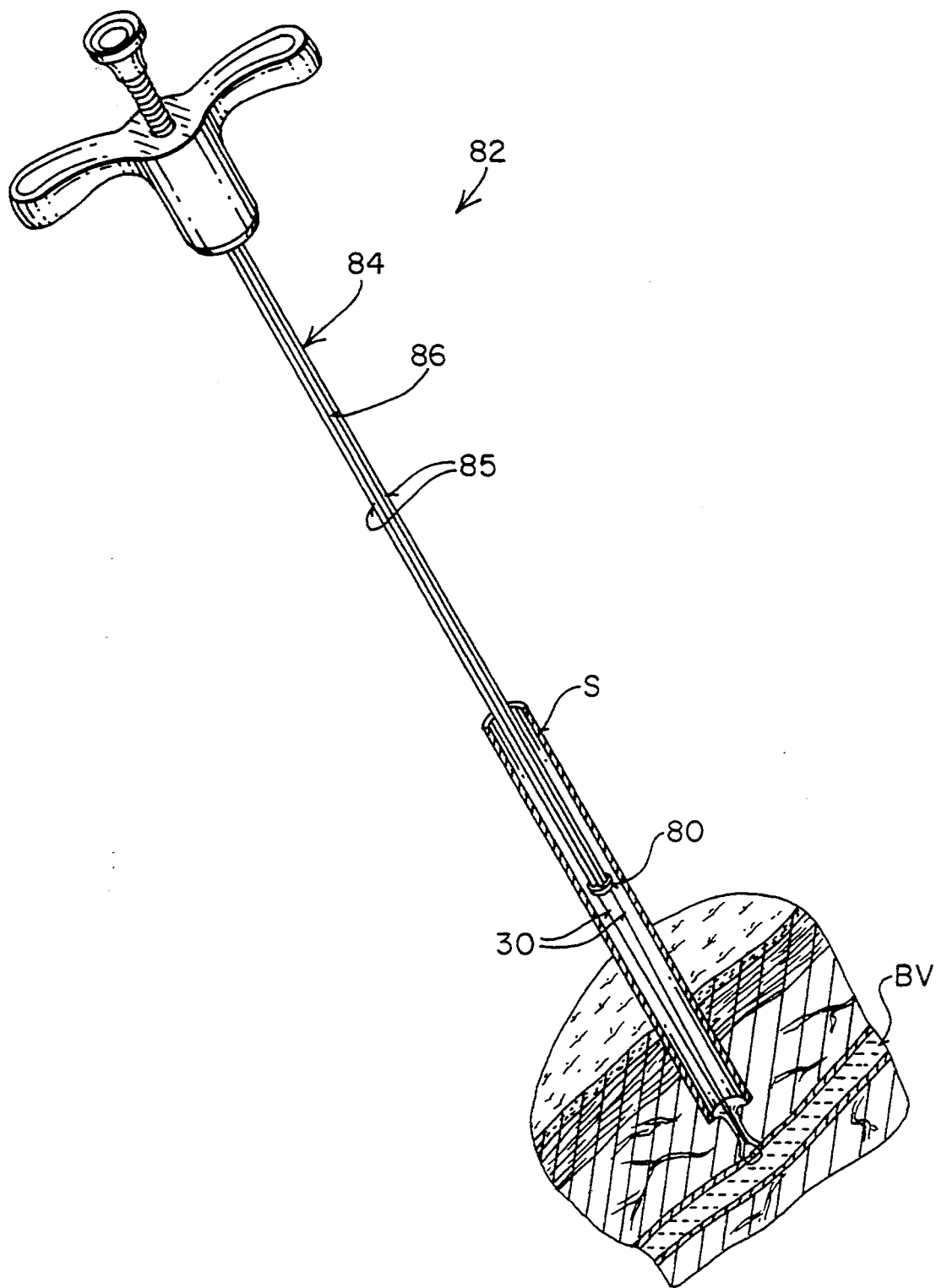
FIG. 13 illustrates a fastener applying device constructed in accordance with the principles of the present invention.

In a preferred option of the present invention, a locking fastener 80 may be inserted over the free ends of the suture 30 using a fastener applier 82, as illustrated in FIG. 13. The locking fastener 80, in combination with a tied suture loop, provides a particularly secure barrier against bleeding, without having the disadvantages of the hemostatic fasteners which have previously been used.

Figure 14:
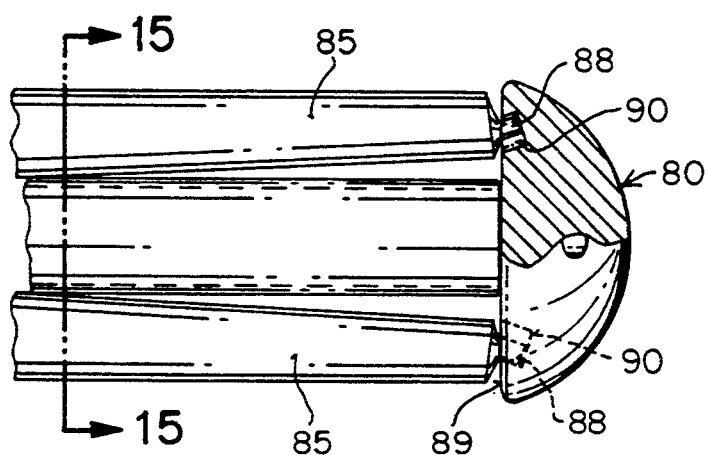
FIG. 14 is a detailed view of the distal end of the fastener applying device of FIG. 13.
Figure 15:
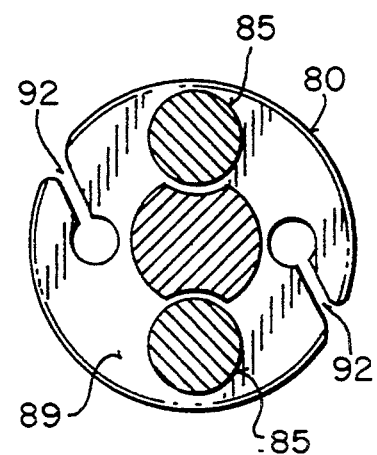
FIG. 15 is a cross-sectional view of the fastener applying device of FIGS. 13 and 14, taken along line 15—15 of FIG. 14.

The fastener applier 82 comprises a shaft 84 including a pair of axial prongs 85 and an axial rod 86. As best illustrated in FIGS. 14 and 15, the axial prongs 85 terminate in outwardly disposed tips 88 which are received in receptacle wells 90 formed in a rear surface 89 of the locking fastener 80. The axial prongs 85 are resilient and tend to spring radially outward, thus allowing the tips 88 to hold the fastener member 80 by engaging the well receptacles 88. The locking fastener 80 can be placed over the ends of suture 30 through slots 92 formed on opposite sides of the fastener.

Figure 16:
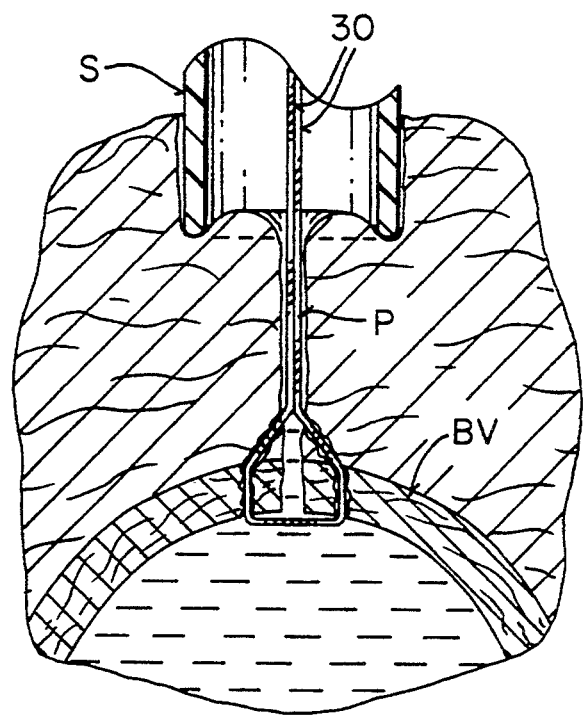
FIGS. 16 and 17 illustrate placement of the fastener in connection with tying of the free ends of the suture and the method of the present invention.
Figure 17:
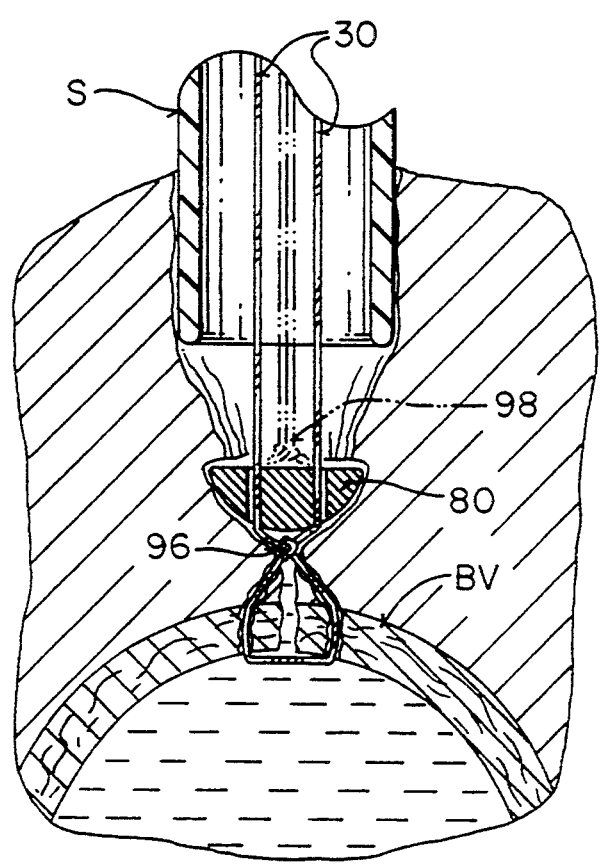

Referring now to FIGS. 16 and 17, after the suture 30 has been drawn out through the tract P and introducer sheath S, fastener 80 is introduced over the suture 30 using the applier 82. Once the fastener 80 is positioned a proper distance over the blood vessel BV, as illustrated in FIG. 17, the suture applier will be rotated to twist the suture, as shown at 96. A knot 98 may then be tied in the remaining free ends of the suture 30 and pushed downward over the fastener 80 to secure the fastener in place.

Figure 18:
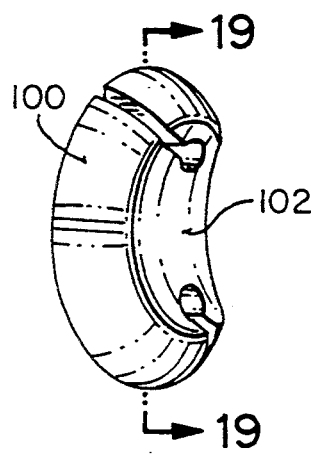
FIGS. 18 and 19 illustrate a first alternative embodiment of the fastener of the present invention.
Figure 20:
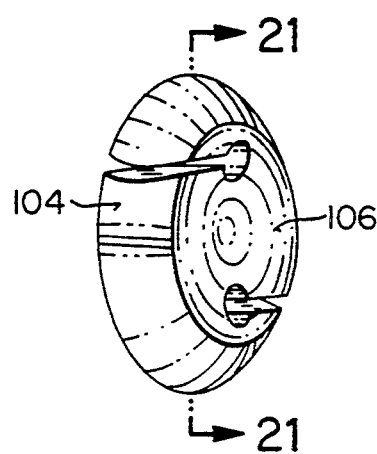
FIGS. 20 and 21 illustrate a second alternative embodiment of the fastener of the present invention.
Figure 22:
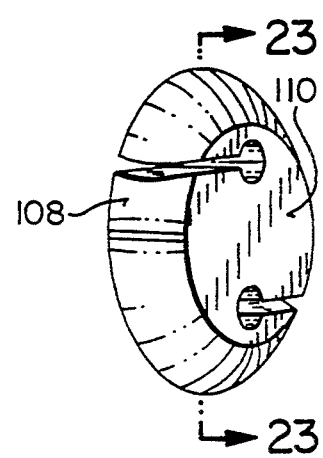
FIGS. 22 and 23 illustrate a third alternative embodiment of the fastener of the present invention.
Figure 19:
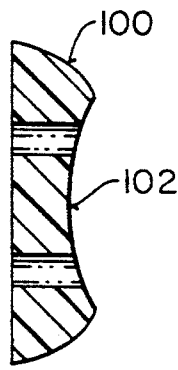
Figure 21:
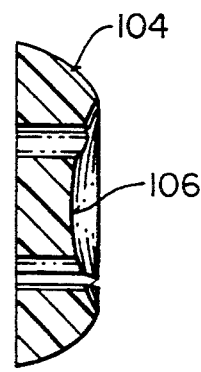
Figure 23:
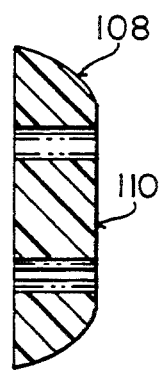

Alternate locking fastener embodiments are illustrated in FIGS. 18–23. In FIGS. 18 and 19, a locking fastener 100 includes a cylindrical cavity 102 which would permit the fastener to be placed closely over the blood vessel. In FIGS. 20 and 21, the fastener 104 includes a concave hemispherical recess 106 which would also permit close placement of the fastener over a blood vessel wall. Finally, in FIGS. 22 and 23, fastener 108 includes a flat face 110 which would also be suitable for use in the present invention.

In addition to tying and use of a fastener, the present invention will encompass other devices and approaches for securing the suture as will be readily apparent to one skilled in the art.

Referring now to FIGS. 24–27, a second embodiment of the suture applying device of the present invention will be described. Suture applying device 200 comprises an introducer sheath 202, a support sheath 204, a capture sleeve 206, a guide sleeve 208, and a needle shaft 210. The capture sleeve 206 will be mounted coaxially over the guide sleeve 208, and the guide sleeve 208 in turn will be mounted coaxially over the needle shaft 210, in order to form a needle advance and capture assembly 212, as illustrated in FIGS. 27A and 27B. The introducer sheath 202 will initially be mounted within the support sheath 204 in order to facilitate introduction of the support sheath into a previously formed percutaneous tract, with only the thinner tip 280 of the introducer projecting into the arteriotomy and the shoulder 281 stopping at or near the superficial wall of the artery. After introduction of the support sheath 204, the introducer sheath 202 will be removed, and the needle advance and capture assembly 212 will be introduced through a lumen of the support sheath, as will be described in more detail hereinafter.

Figure 24:
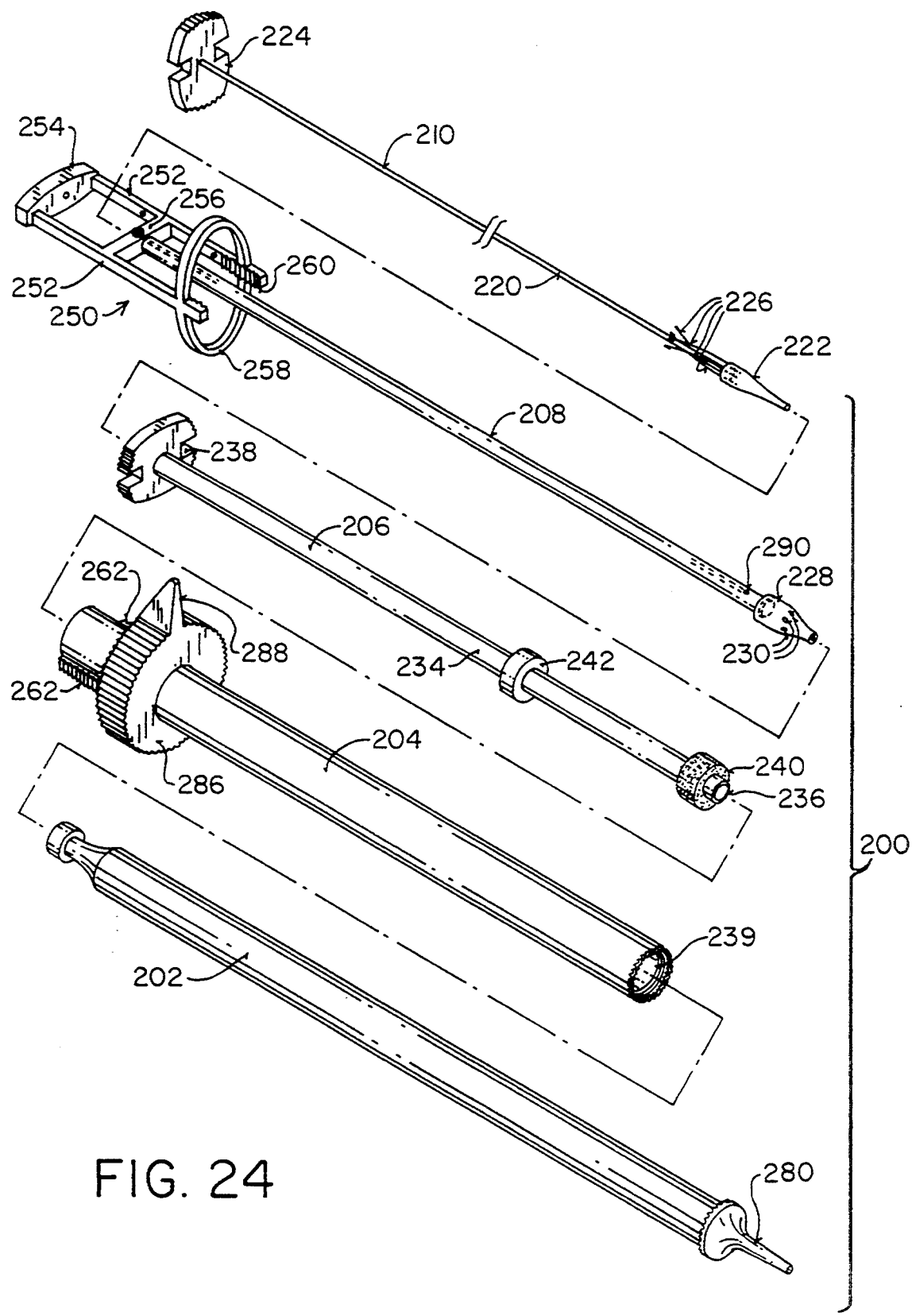
FIG. 24 is an exploded view of a second embodiment of a suturing device constructed in accordance with the principles of the present invention.
Figure 27A:
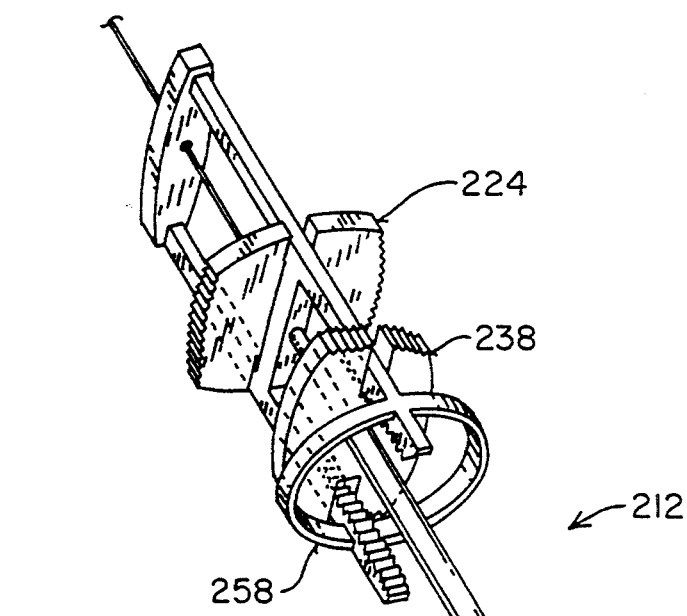
FIG. 27A is a perspective view of the suturing device of FIG. 24, shown in an assembled configuration.
Figure 27B:
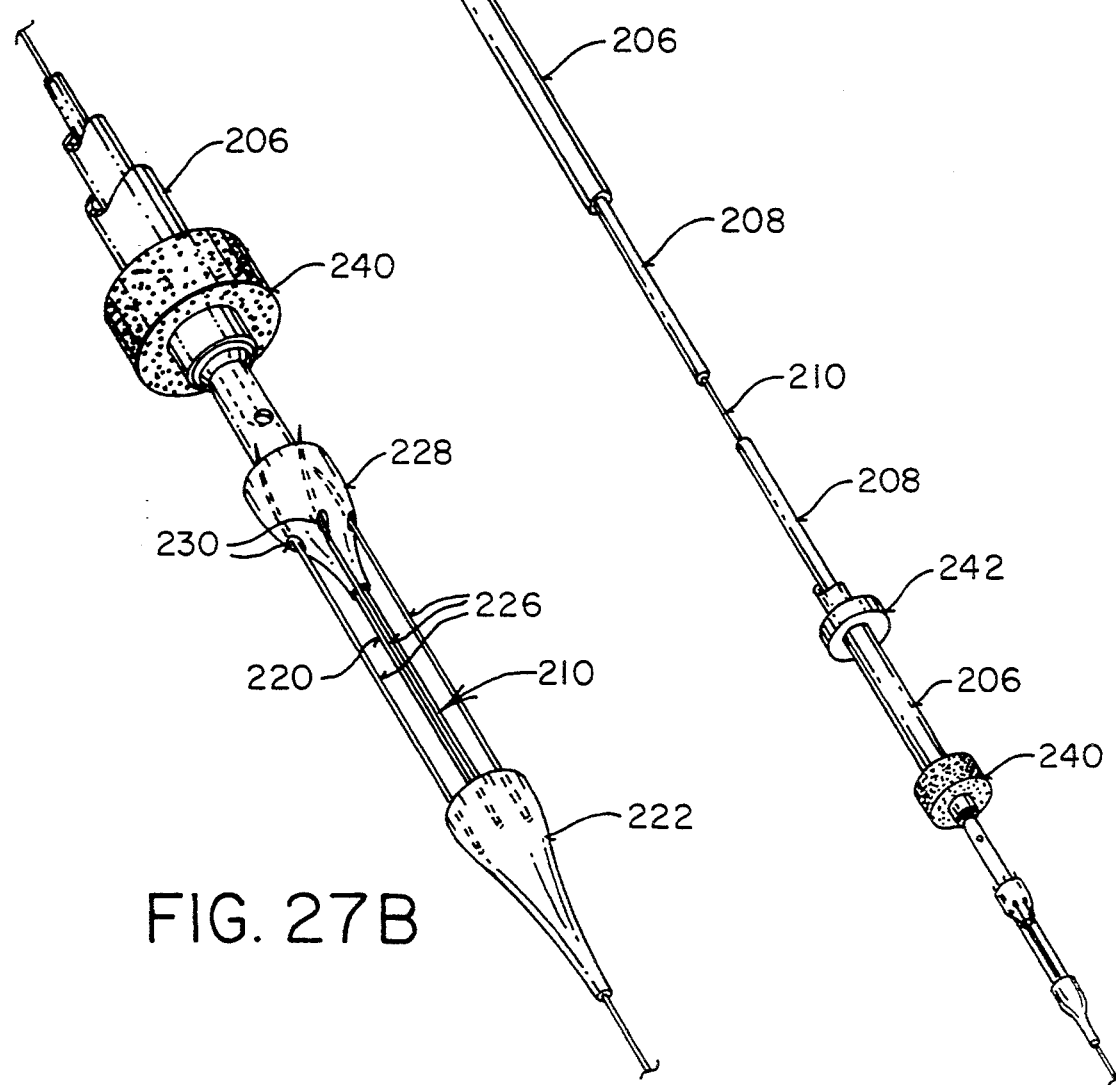
FIG. 27B is an enlarged detail view of the distal tip of the suturing device illustrated in FIG. 27A.
Figure 31B:
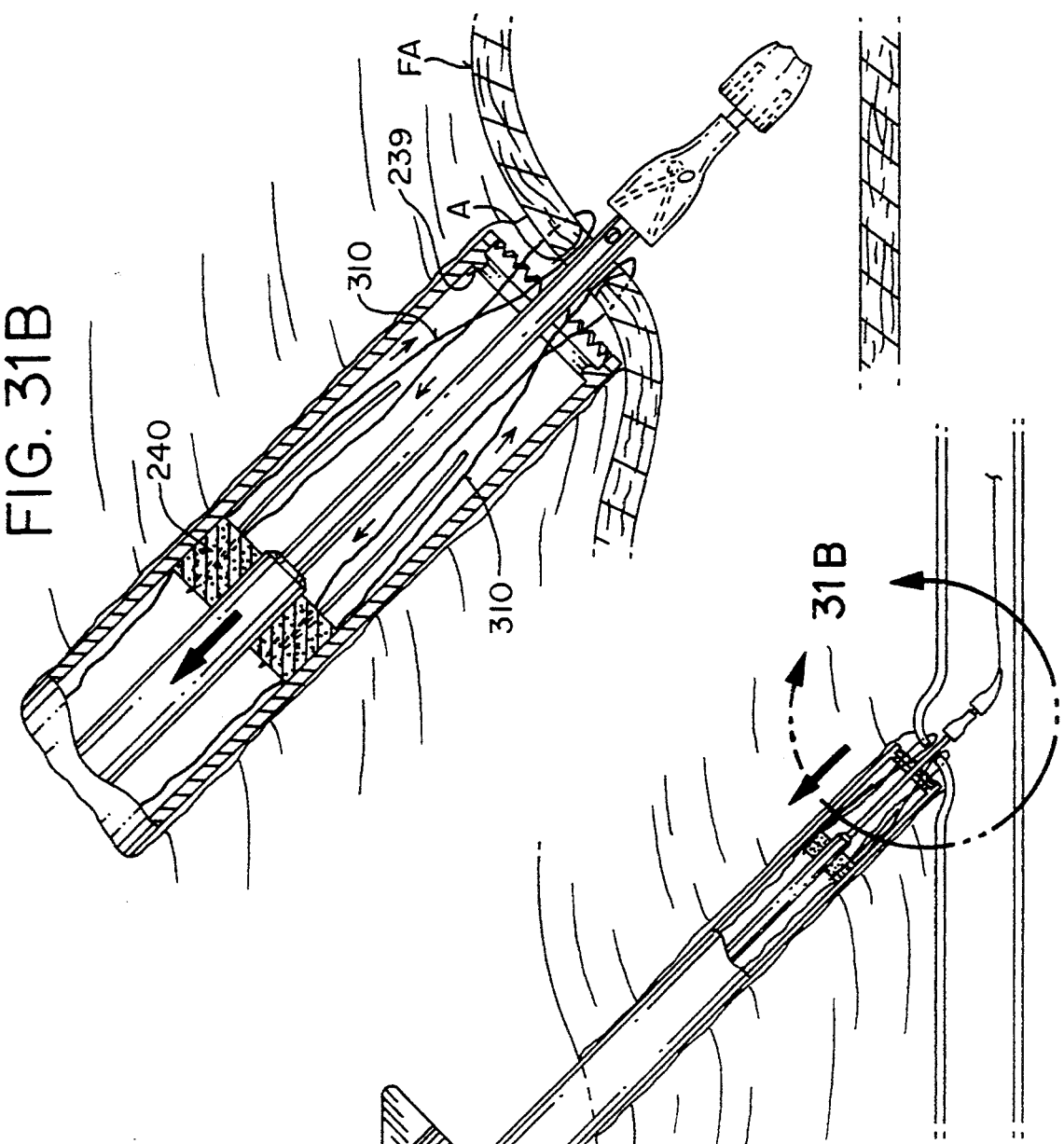
FIG. 31B is a detail view of the distal end of the suturing device, as illustrated in FIG. 31A.
Figure 31A:
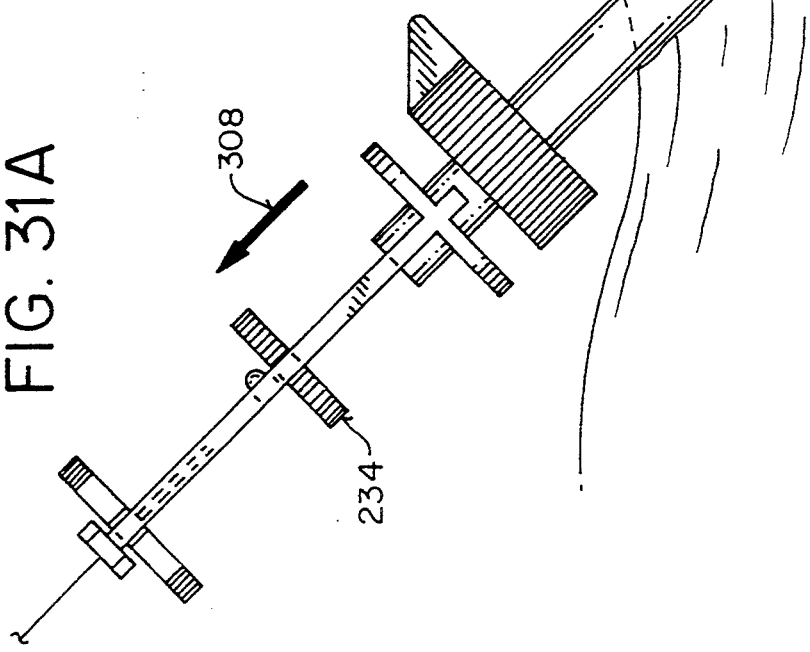
FIG. 31A shows the needles after they have been captured on the shaft of the suturing device and have been partially withdrawn through the sheath.

Referring now to FIGS. 24 and 27B, the needle holder 210 comprises an elongate rod 220 having a needle support holster 222 at a distal end thereof and a knob 224 at a proximal end thereof. The needle support holster 222 carries at least one pair of opposed needles 226, usually carrying two pair of opposed needles as illustrated. As best observed in FIG. 27B, the needles 226 will initially be held at their proximal ends in the support holster 222 with their distal ends being positioned in a guide member 228 secured to the distal end of the guide sleeve 208. It will be appreciated that the needles 226 can thus be advanced proximally (i.e., in an upward direction as illustrated in FIG. 27B) by drawing the needle shaft 210 proximally relative to the guide sleeve 208.

The guide member 228 includes a plurality of guide channels or lumens 230 for receiving the needles 26. The guide channels 230 will be oriented so that the needles 226 are deflected radially outward relative to the needle advance and capture assembly 212 as the needles are advanced proximally relative to the guide sleeve 208. Such radial deflection assures that the needles will penetrate tissue away from the arteriotomy, as best observed in FIG. 30B, described hereinafter.

The needles 226 will typically be formed of a very resilient metal, which will allow the needles to negotiate the relatively sharp bend leading into the arterial lumen of the femoral artery FA, as best seen in FIG. 29. In particular, the needles will be configured in a straight shape but will be able to bend into a slightly arcuate path after crossing the tissue to be sutured and then being deflected inwardly back into the lumen of support sheath 204 by a ridge 239 on the inner wall of support sheath 204, where they will be captured on the capture sleeve 206, as described in more detail hereinafter. A preferred material for fabricating the needles is a nickel-titanium alloy in its superelastic condition, but a high tensile strength stainless steel may also be used.

The capture sleeve 208 comprises a cylindrical body 234 having a central lumen extending from an open distal aperture 236 to a proximal handle 238. The guide sleeve 208 will be slidably received within the lumen of the capture sleeve 206, with the guide member 228 extending out of the open distal aperture 236, as best observed in FIGS. 27A and 27B. The capture sleeve 206 includes a capture target 240 which is conveniently an annular disk secured to the exterior of the sleeve. The capture target 240 may be composed of any material which is easily penetrable by the needles 226 and which can serve to capture the distal ends of the needles so that they may be drawn outwardly by the target as the capture sleeve 206 is pulled via handle 238 so as to disengage needles 226 from support holster 222 and pull needles 226 through guide member 228 and clear of arterial tissue of the femoral artery FA surrounding the puncture site and into the lumen of support sheath 204 as described hereinafter. A second annular disk 242 is provided on the sleeve 206 proximally of the capture target 240, to assist in centering capture sleeve 206 within support sheath 204. Suitable materials for these components include nylon, delrin, polycarbonate, and other moldable or extrudable materials.

Figure 25:
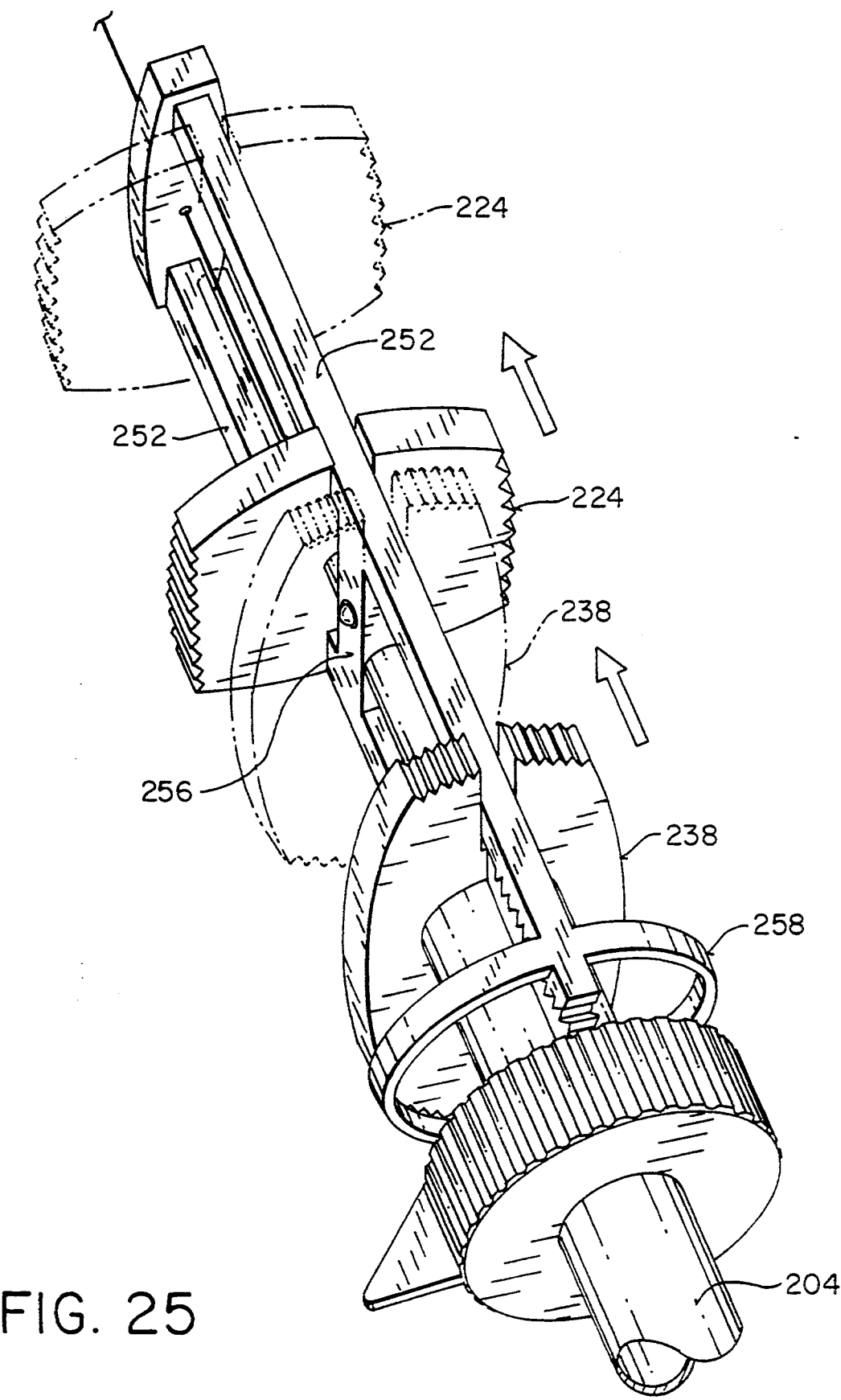
FIG. 25 is an enlarged view of the proximal end of the suturing device of FIG. 24.
Figure 26A:
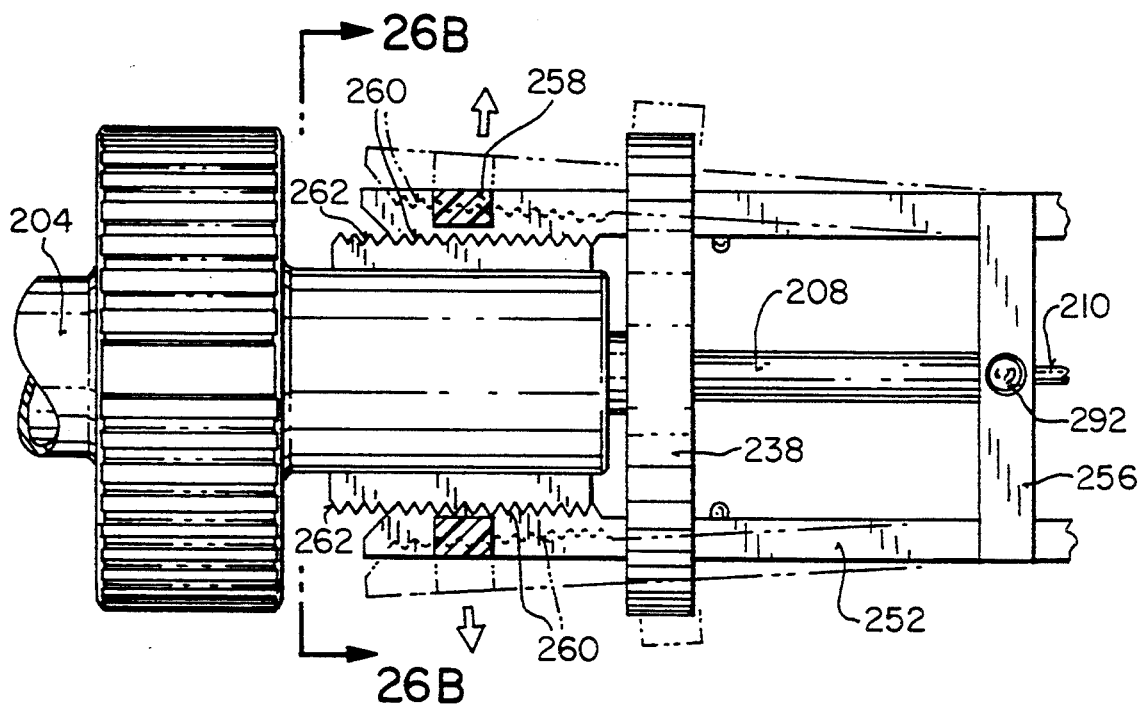
FIG. 26A is an enlarged elevational view of a portion of the proximal end of the device illustrated in FIG. 25.
Figure 26B:
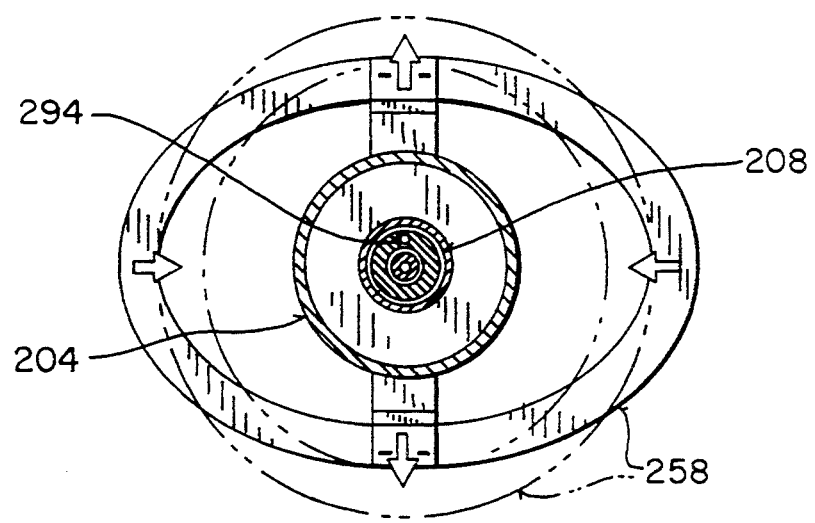
FIG. 26B is a cross-sectional view taken along line 26B—26B in FIG. 26A.

Referring now also to FIGS. 25, 26A, and 26B, the proximal end of guide sleeve 208 includes a cage structure 250 having an H-frame which comprises parallel axial tracks 252, a top bar 254, and a middle bar 256. An elliptical or oblong ring 258 is part of the distal ends of the parallel tracks 252 in such a way that the tracks can be spread apart (as illustrated in FIG. 26A) with the ring acting as a spring. Conveniently, the user may spread the tracks 252 apart by compressing the elliptical ring 258 along the longer elliptical axis. The inner surfaces of the distal portions of parallel tracks 252 comprise gear teeth 260 which mate with gear teeth 262 on a proximal end of the support sheath 204. It will be appreciated that the gear teeth 260 and 262 will mesh to hold guide sleeve 208 in a fixed position relative to the support sheath 204 at all times except when the parallel tracks 252 are spread apart by compressing the elliptical ring 258. As described in more detail hereinafter, this feature allows the user to introduce the needle advance and capture assembly 212 to a desired depth relative to the support sheath 204 and thereafter leave the assembly at the desired position until it is time to remove the entire capture assembly 212.

Prior to use, the needle advance and capture assembly 212 will be in the configuration illustrated in FIGS. 25, 27A and 27B. That is, the needle shaft 210 will be in its most distal position relative to the guide sleeve 208. Knob 224 attached to needle shaft 210 will lie adjacent the middle bar 256 of the cage structure 250. The capture sleeve 206 will lie in its most proximal position relative to the guide sleeve 208, with knob 238 lying adjacent the elliptical ring 258. In use, it will be appreciated that the needle shaft 210 will first be drawn proximally via the handle 224 in order to pass the needles 226 through the site to be sutured, and into engagement with the capture target 240 which is an integral part of capture sleeve 206 to effect capture of needles 226. Such a method will now be described in greater detail in connection with FIGS. 28-33.

The method of utilizing device 200 begins by inserting the support sheath 204 having introducer sheath 202 in place within its central lumen. The introducer sheath 202 defines a tapered end 280 which may be introduced over a guidewire 282 which has previously been placed in the percutaneous tract P and the puncture site A through the femoral artery FA as part of an earlier procedure. A proximal end 284 of the introducer sheath 202 extends outward from the proximal end of the support sheath 204, and the introducer sheath will be composed of a resilient material which allows the introducer sheath to be collapsed and withdrawn from the support sheath after the support sheath is properly positioned. Conveniently, the distal end of the support sheath 204 will have a serrated edge in order to help anchor the support sheath in place within the tract P and centered around the puncture site. As illustrated in FIG. 28, the support sheath 204 includes a manipulation knob 286 having a pointer 288 near its proximal end. The manipulation knob 286 allows the user to manipulate the combination of support sheath 204 and introducer sheath 202 as they are being positioned within the tract P. The pointer 288 will be oriented in a predetermined direction relative to the patient in order to facilitate positioning following the remaining steps of the method. Typically, the pointer 288 will be oriented toward the patient's head in a conventional cardiac interventional procedure accessed through a femoral arteriotomy.

Referring now to FIG. 29, the needle advance and capture assembly 212 will be introduced to the support sheath 204 after the introducer sheath 202 has been withdrawn. The assembly 212 will be inserted into the support sheath 204 until the guide member 228 on the guide sleeve 208 enters the lumen of the femoral artery FA through the arteriotomy A. To assist the user in determining when the guide member has entered the femoral artery FA, a blood inlet port 290 (best observed in FIGS. 24 and 30) is provided near the distal end of the guide sleeve 208. Port 290 is connected to a viewing port 292 through a lumen 294 (FIG. 26B). The viewing port 292 incorporates a small vent (not shown) so that air may easily be expelled from the lumen 294 to permit blood flow to reach the viewing port, but is sufficiently small to restrict the outward flow of blood from the viewing port. Thus, the user will be able to see blood appear at the viewing port 292 as soon as the guide member 228 has entered the femoral artery FA. At that point, the user can stop insertion. The assembly 212 will be held in place relative to the support sheath 204 through the meshing of teeth 260 and 262 as described previously.

With the needle advance and capture assembly 212 being fully introduced through the support sheath 204, the needles 226 will be fully introduced into the femoral artery FA. In particular, the tips of the needles will lie on the superficial side of the arteriotomy in the artery wall.

Referring now to FIG. 30A and 30B, the needles 226 will be drawn proximally through the wall of femoral artery FA by pulling knob 224 in a proximal direction relative to the remainder of the device, as illustrated by arrow 300 in FIG. 30A. The knob 224 will draw the needle shaft 210 in the proximal direction which in turn causes the needle support holster 222 to push the needles in the direction of arrows 302 and 304. The needle guide member 228 causes the needles 226 to flare radially outward so that they pass through the blood vessel wall, and into engagement with the capture target 240 within the lumen of the support sheath 204 as illustrated in FIG. 30B.

The suture 310 (FIG. 31B) carried between adjacent pairs of needles 226 will then be drawn downward through the support sheath 204, through the gap between the arteriotomy A in the femoral artery FA and the guide sleeve 208, through the punctures left by needles 226, and finally out through the lumen of the support sheath as the needles are first moved partly outward by the action of knob 234, and then carried outward by the target 240 with the removal of the entire capture assembly 212 from support sheath 204.

Figure 32:
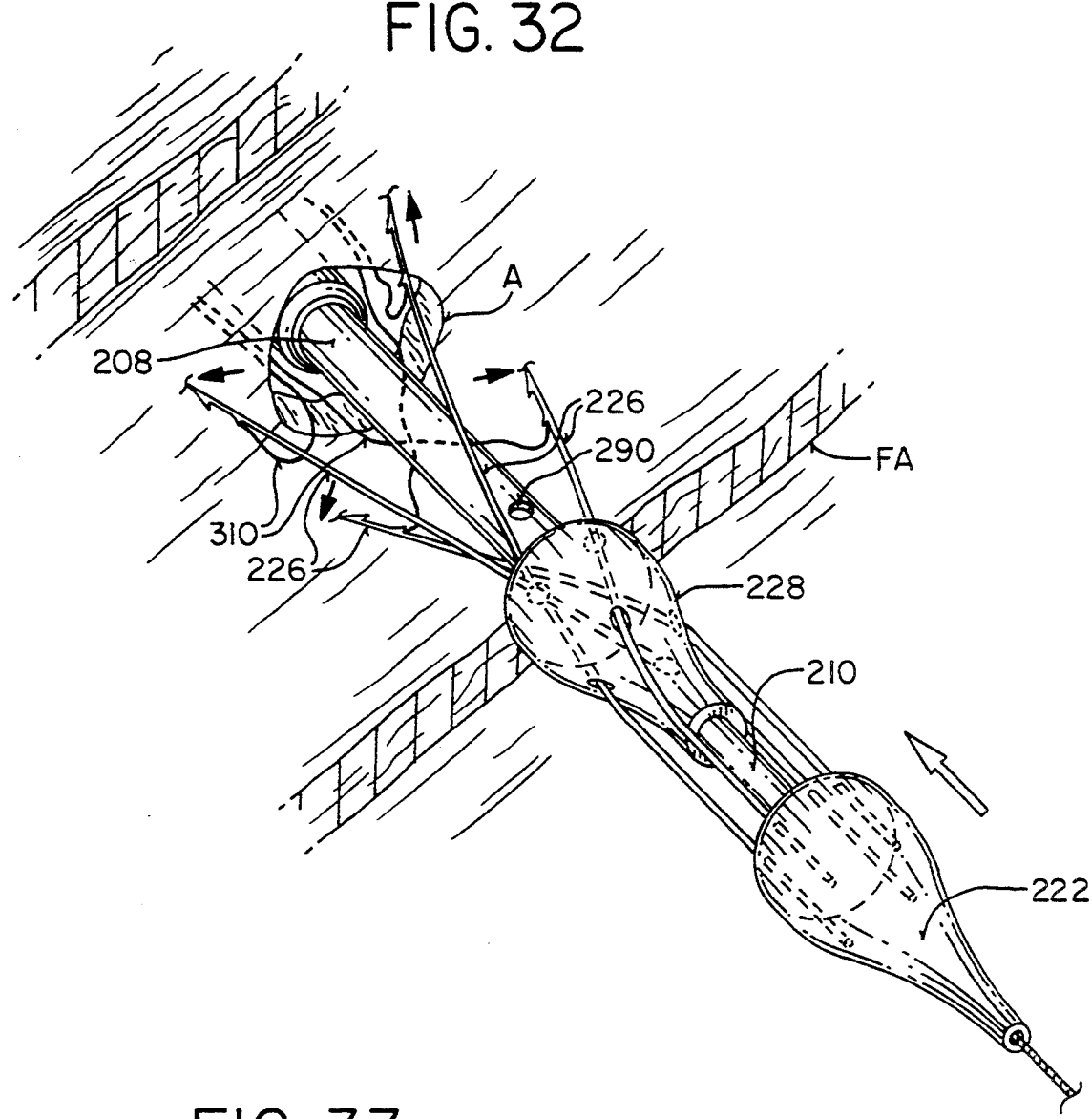
FIG. 32 is a perspective view from inside a blood vessel illustrating the geometry of the needle penetration afforded by the needle guide carried at the distal end of the shaft of the suturing device of the present invention.
Figure 33:
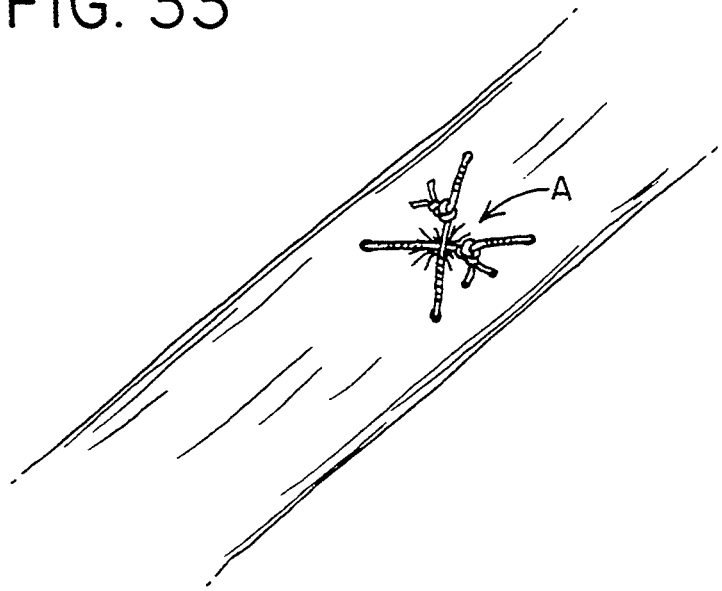
FIG. 33 illustrates the X-pattern of the tied suture applied by the suturing device.

Referring now to FIG. 32, the preferred pattern of four needles being delivered by the needle support holster 222, through the needle guide member 228, and into the wall of the femoral artery FA is illustrated. It can be seen that the guide member 228 deflects the needles radially outward so that the pattern of four needles engages the artery wall in an approximately square pattern about the arteriotomy A. After the sutures are tied and the knots advanced back through the support sheath 204, the resulting pattern of tied suture will appear as in FIG. 33 when viewed towards adventitial surface of the femoral artery FA surrounding the arteriotomy A.

Figure 34:
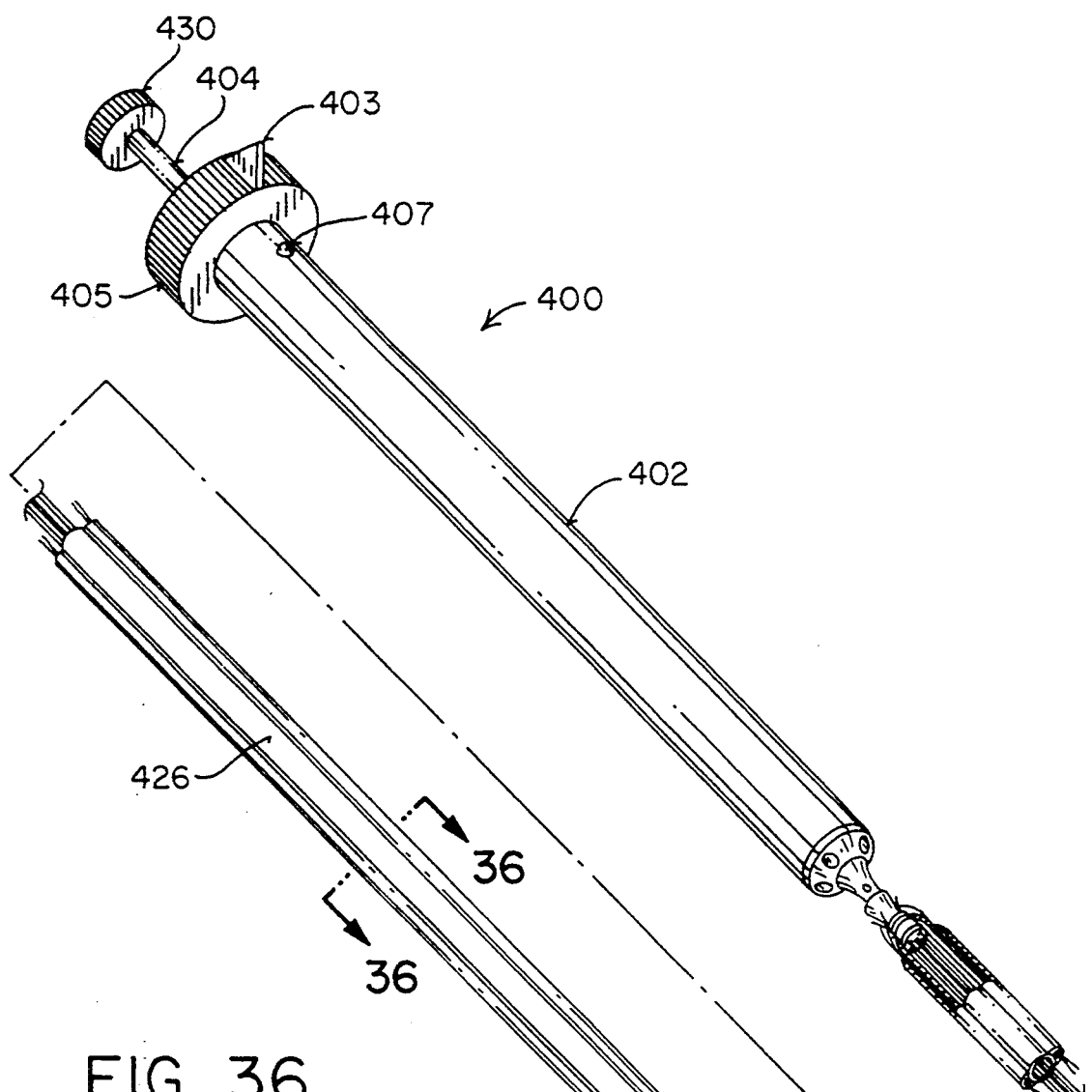
FIG. 34 is a perspective view of a second alternate embodiment of a suturing device constructed in accordance with the principles of the present invention.
Figure 36:
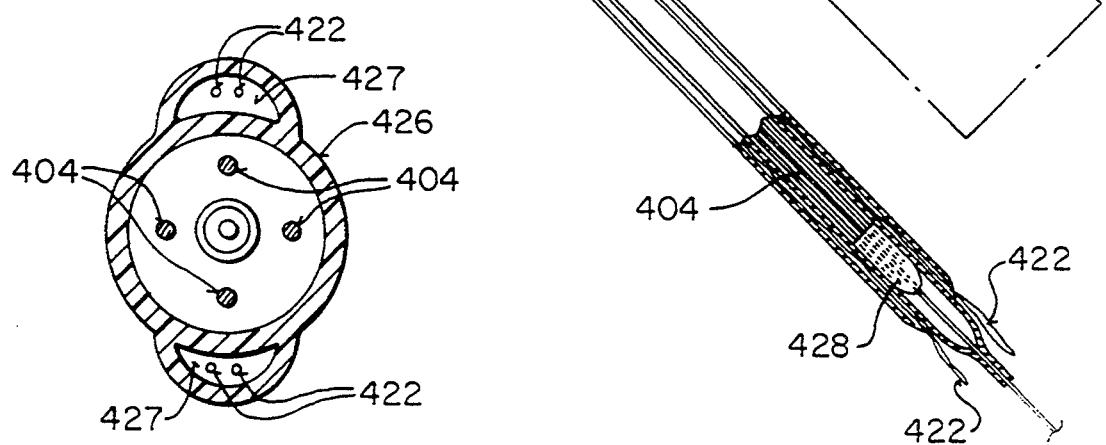
FIG. 36 is a cross-sectional view of the device of FIGS. 35A and 35B, taken along line 36—36 of FIG. 35B.
Figure 35A:
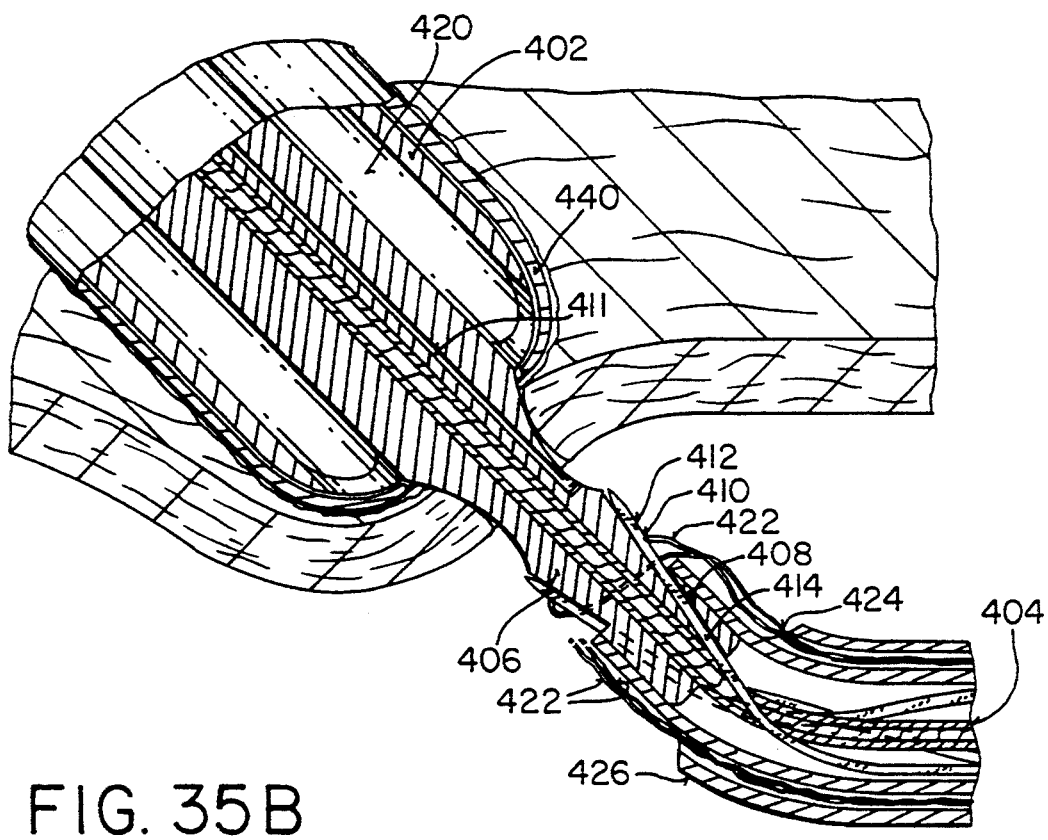
FIG. 35A is a detail view of the distal end of the guide body of the suturing device of FIG. 34, shown with the needles retracted fully within the guide body.
Figure 35B:
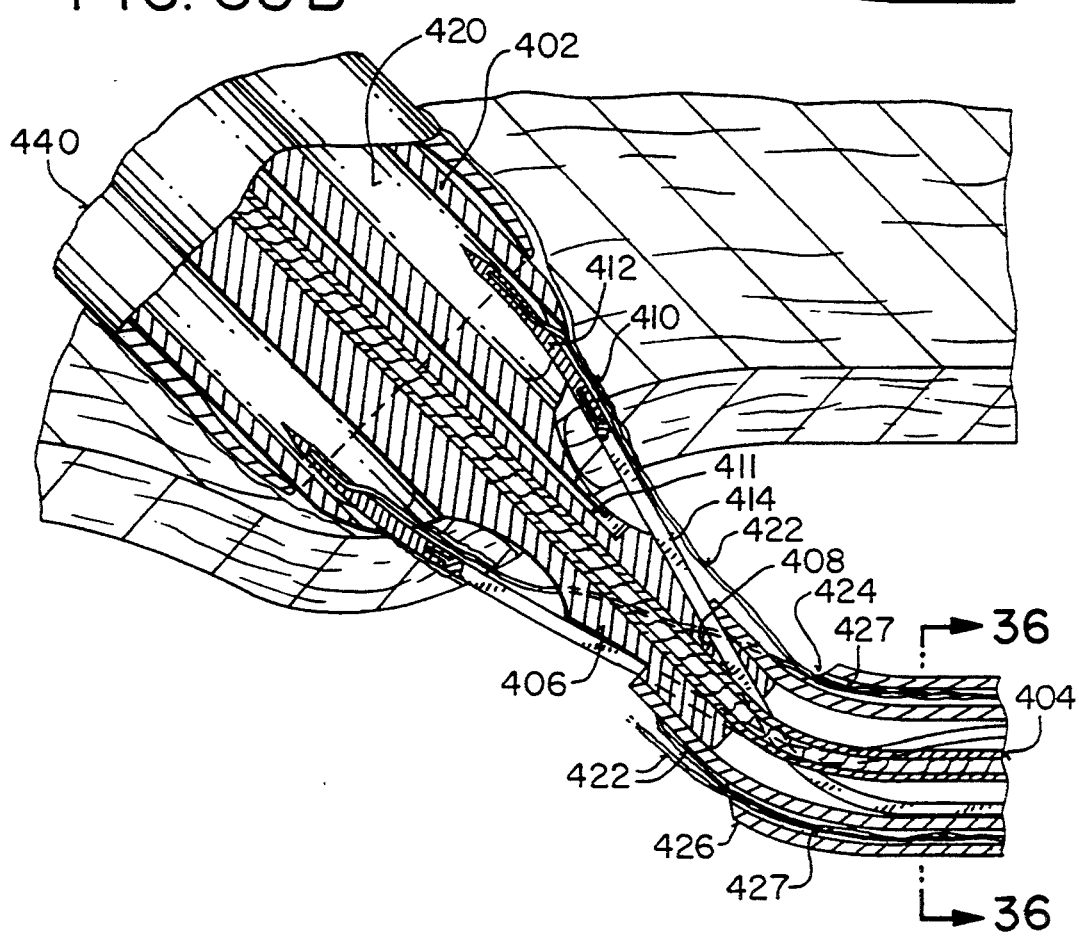
FIG. 35B is a view similar to FIG. 35A, except that the needles have been partially drawn back into the guide body.

A third embodiment of the suture applying device of the present invention is illustrated in FIGS. 34–36. The device 400 comprises a guide body 402 and a needle shaft 404. The guide body 402 includes a guide tip 406 at its distal end, which guide tip includes a plurality of guide channels 408 which receive the proximal ends of needles 410. An aligning arrow 403 is mounted on handle 405 located at the proximal end of the guide body 402. A marker lumen bubble 407 is located below the aligning arrow and serves to indicate when the distal end of the guide body has entered a blood vessel, as described in connection with previous embodiments. An indicator lumen 411 which permits the flow of blood to the marker lumen bubble 407 is illustrated in FIGS. 35A and 35B.

The needles 410 as illustrated comprise a sharpened tip section 412 and an elongate shank portion 414, but may also be manufactured as an integral piece. The shank portion 414 will be sufficiently long so that the needles may be pushed from their butt end by a support holster 428 fixedly attached to the needle shaft 404 in order to advance the needles through the tissue to be sutured and fully through the guide body 402 inserted together with support sheath 440 in the associated tract so that no capture mechanism will be required, as with previous embodiments.

The guide body 402 further includes a plurality of needle lumens 420 which are axially aligned and spaced about the periphery of the guide body. As best seen in FIG. 35B, the needles 410 will enter the distal ends of the lumens 420 as the needles are advanced proximally relative to the guide body.

A flexible needle sheath 426 will be attached to the guide tip 406 of guide body 402. The central lumen of the needle sheath 426 receives a support holster 428 attached to the distal end of the needle shaft 404, as well as the needles 410. As with previous embodiments, the butts of the needles 410 are removably received within the support holster 428. The sheath 426 will be sufficiently long to permit the needles to extend at least 5 cm beyond the distal end of guide body 402.

Prior to use, the suture applying device 400 will be in the configuration illustrated in FIGS. 34 and 35A. That is, the needle shaft 404 will be distally positioned within the guide body 402 and needle sheath 426. In particular, the tips of needles 412 will lie just at the guide tip 406 so that they may be easily advanced through the arterial tissue surrounding the arteriotomy. That is, the tips of the needles will be generally retracted within the guide tip 406. A length of suture 422 is attached to the proximal tips 412 of opposed pairs of needles 410, with the connecting suture being stored in side lumens 427 extending axially along the exterior of the needle sheath 426. As best observed in FIGS. 35A and 35B, the suture 422 extending between one pair of opposed needles is received in a first of the side lumens 427, while the suture extending between the other pair of opposed needles is received in the second of the side lumens. While it would be possible to store the suture 422 in the lumens 420 of the guide body 402 (and thus eliminate the need for side lumens 427), such storage is less preferred since it increases the risk that the suture will become entangled with the needles 410 as they are withdrawn proximally. The use of side lumens 427 greatly simplifies feeding of the suture as the needles 410 are withdrawn.

After the guide tip 406 has been past through the puncture site to be sutured, the needles may then be drawn proximally forward through the tissue to be sutured by drawing proximally on handle 430 at the proximal end of needle shaft 404. The method of the present invention will now be described in more detail with reference to FIGS. 37-41.

Figure 37:
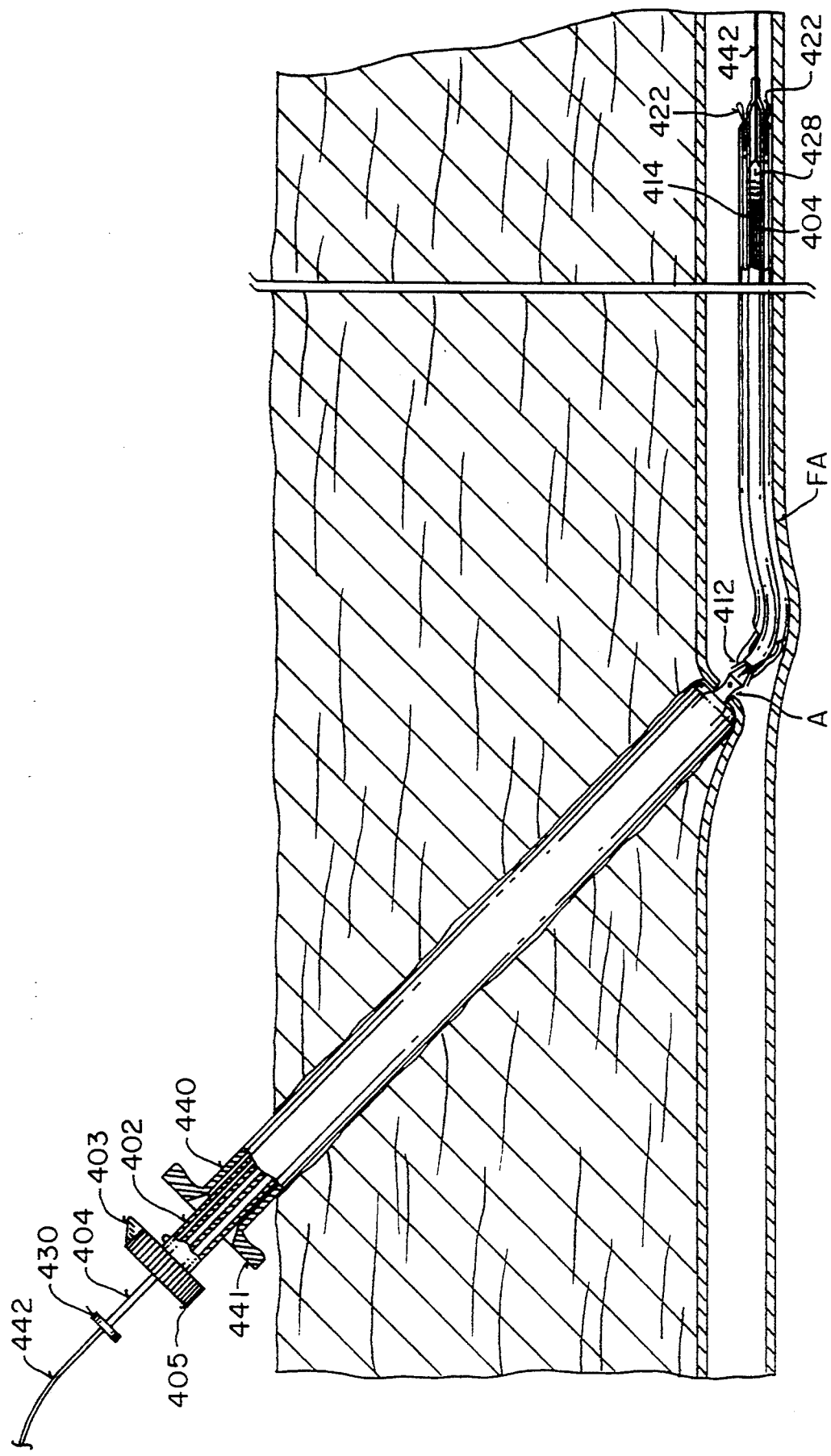
FIGS. 37-40 illustrate the method of the present invention using the suturing device of FIG. 34.
Figure 38:
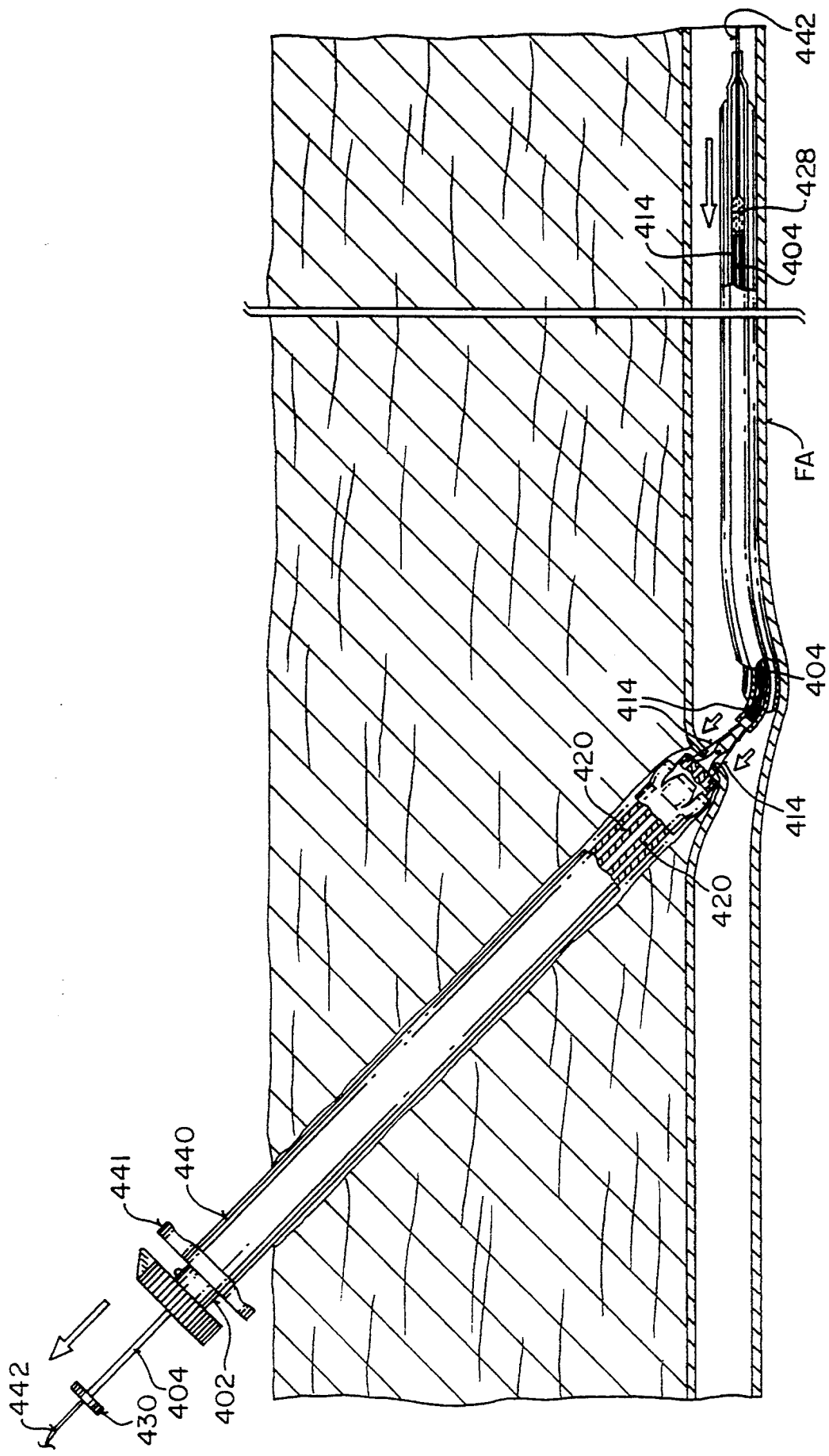
Figure 40:
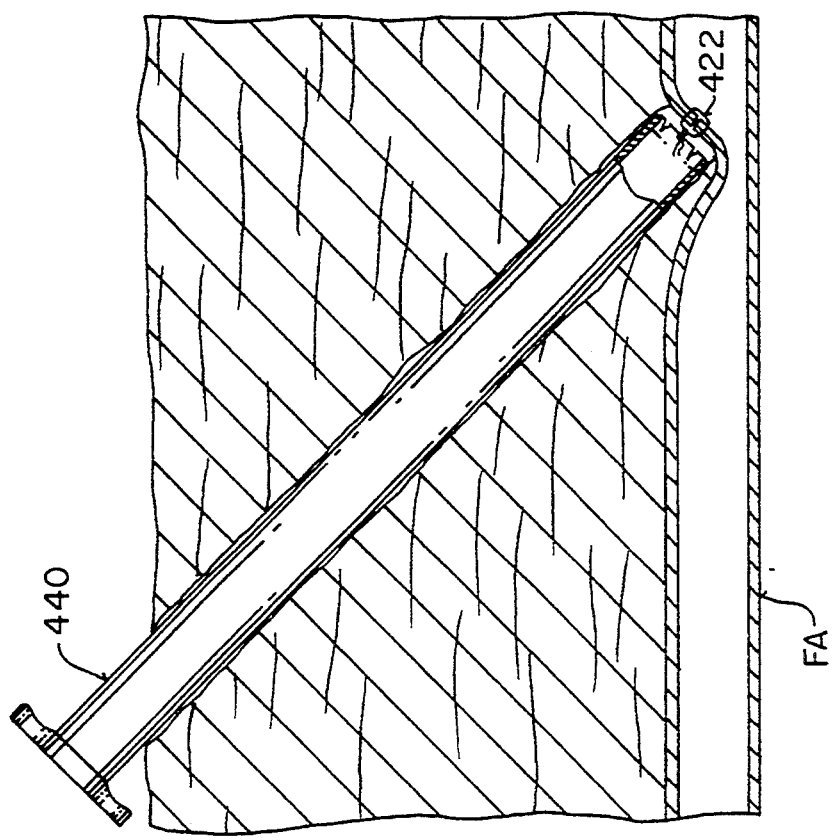
Figure 39:
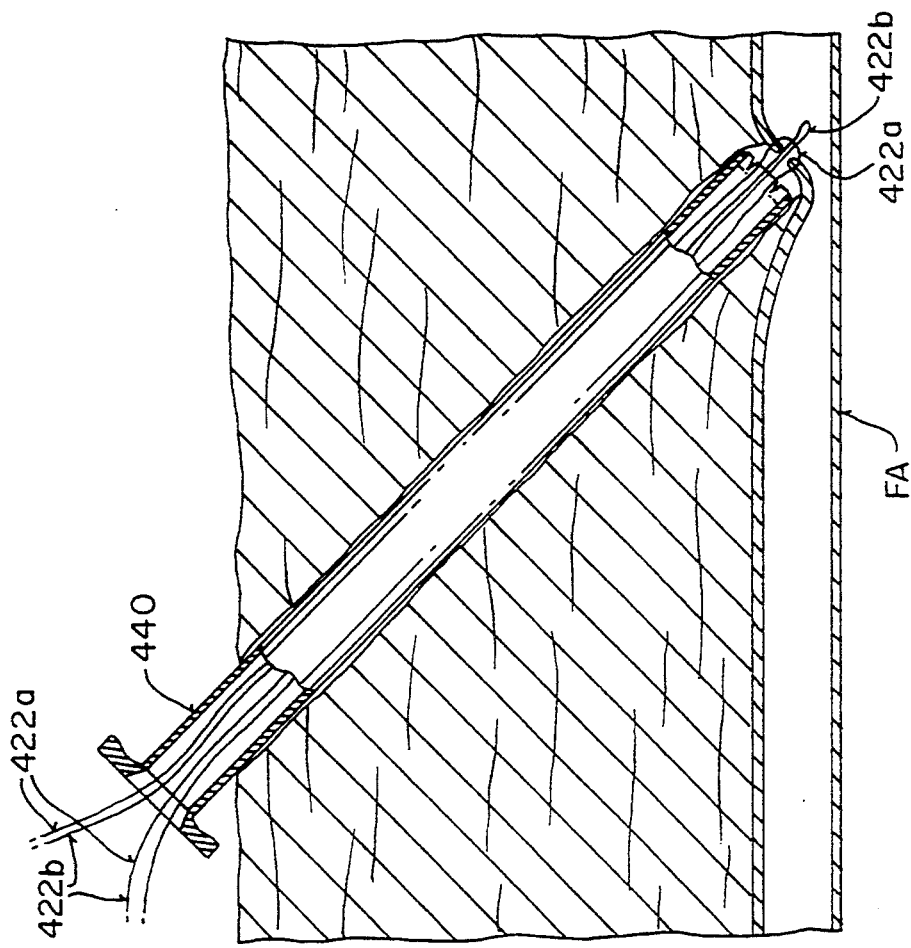

The situation following an interventional or other vascular procedure, where the attending physician is satisfied that the puncture site may be sealed, is illustrated in FIG. 37. A conventional introducer sheath is in place with a guidewire passing into the femoral artery. The conventional introducer sheath is withdrawn after assuring that an appropriate guidewire for the suturing process is in place. The device 400 (including a support sheath 440 which initially covers the ports to the needle lumens 420) will then be introduced over the guidewire, as illustrated in FIG. 37. The needles 410 and sutures 422 mostly encased by flexible needle sheath 426, will be fully advanced into the femoral artery FA past the arterial puncture site A. Handle 441 on support sheath 440 is then partially withdrawn proximally to expose the needle lumens 420 (as shown in FIGS. 35A, 35B, and 38. Handle 430 will then be drawn proximally outward relative to the guide body 402, causing the needles 410 to pass through the superficial wall of the femoral artery FA and into the needle lumens 420, as illustrated in FIGS. 35B and 38. The handle 430 may continue to be drawn proximally (i.e., outward from the patient) in order to continue to pull the needle shaft 404 through the guide body 402. Such movement of the needle shaft 404, in turn, continues to draw the needles 410 outward through the lumens 420 of the guide body 402 until the tips of the needles are exposed. The user may then grasp the needles and continue to draw them out until the suture is available to the user. The guide body 402 may then be withdrawn from the support sheath 440, leaving a portion of the needle sheath 426 still in the puncture site A to maintain hemostasis. The suture can then be tied and the knot pushed back down through the support sheath 440. The knot will then only be tightened when the needle sheath is finally withdrawn from the puncture site A.

Device 400 has certain advantages over the previous embodiments. Since it is not necessary to capture the needles using an internal capture mechanism, the needles need not have barbs. Such barbless needles will minimize trauma to the arterial tissue around the puncture site A and simplify the procedure. The guide body 402 and guide tip 406 are designed as an integral structure to assure that needles 410 will be precisely centered around the puncture site A, and will very reliably enter the needle lumens 420 in guide body 402. Also, tip 406 will occlude the arteriotomy puncture during the performance of the procedure, providing hemostasis. Moreover, the entire procedure is simplified, with fewer discrete steps being performed. The user need only introduce the device over-the-wire and thereafter draw out the needle shaft to carry the needles through the tissue to be sutured and outward through the guide body, where the suture becomes accessible and may be tied in a conventional manner.

Although the foregoing invention has been described in detail for purposes of clarity of understanding, it will be obvious that certain modifications may be practiced within the scope of the appended claims.

What is claimed is:

1. A method for suturing a puncture site, said method comprising:
   introducing a shaft inwardly through the puncture site located at the distal end of a tissue tract;
   positioning a pair of needles having a length of suture therebetween carried by the shaft so that they engage tissue on opposite sides of the puncture site;
   drawing the shaft outwardly through the puncture site to simultaneously push free ends of the needles through the tissue;
   guiding the needles through the tissue, into the tissue tract, and outward so that the free ends of the needles emerge through the tissue tract while proximal ends of the needles remain on the shaft;
   pulling the free ends of the needle to remove the needles from the shaft;
   withdrawing the shaft and the needles from the puncture site and tract to expose free ends of the suture; and
   securing free ends of the suture to close the puncture site.

2. A method as in claim 1, wherein the step of positioning includes positioning the pair of needles on opposite sides of a percutaneous penetration to a blood vessel lumen.

3. A method as in claim 2, wherein introducing the shaft comprises introducing the shaft to the blood vessel lumen through an introducer sheath.

4. A method as in claim 1, wherein the tips of the needles are pulled manually.

5. A method as in claim 1, wherein securing the free ends of the suture comprises tying said free ends into a knot.

6. A method as in claim 1, wherein securing the free ends of the suture comprises introducing a fastener over the free ends of the suture.

7. A method for suturing a puncture site in a blood vessel wall, said method comprising:
   introducing a shaft inwardly through a tissue tract to the puncture site;
   positioning a pair of needles carried by the shaft so that they engage the blood vessel wall on opposite sides of the puncture site;
   drawing the shaft outwardly through the tissue tract to simultaneously push free ends of the needles through the blood vessel wall and into the tissue tract;

pulling the free ends of the needle to remove the needles from the shaft after said free ends of the needles emerge from the tissue tract;

withdrawing the shaft and the needles from the tissue tract to expose free ends of the suture; and securing free ends of the suture to close the puncture site.

8. A method as in claim 7, wherein introducing the shaft comprises introducing the shaft to the blood vessel lumen through an introducer sheath.

9. A method as in claim 7, wherein the tips of the needles are pulled manually.

10. A method as in claim 7, wherein securing the free ends of the suture comprises tying said free ends into a knot.

11. A method as in claim 10, wherein securing the free ends of the suture comprises introducing a fastener over the free ends of the suture.

12. A suturing device comprising:
a guide body having a proximal end and a distal end;
a shaft having a proximal end and a distal end, said shaft being slidably mounted in the guide body;
a pair of needles removably carried near the distal end of the shaft, wherein each needle includes a shank and a sharpened tip with the shank carried on the shaft and the tip disposed toward the proximal end of the shaft;
a length of suture secured to and extending between the needles;
means on the guide body for receiving the needles and passing said needle to the proximal end of the guide body as said needles are drawn proximally by said shaft; and
means near the distal end of the guide body for guiding the needles through tissue and to the needle receiving means as said needles are drawn proximally by said shaft.

13. A suturing device as in claim 12, wherein the shaft and the needles are flexible and at least as long as the guide body.

14. A suturing device as in claim 13, wherein the means for guiding the needles comprises a guide tip fixed at the distal end of the guide body and having guide channels for receiving the flexible needles.

15. A suturing device as in claim 14, further comprising a flexible sheath attached to and extending distally from the guide tip, wherein said sheath receives the flexible needles and shaft prior to the needles and shaft being drawn proximally into the guide body.

16. A suturing device as in claim 13, wherein the means for receiving comprises axial lumens formed in the guide body which receive the needles as the shaft is drawn proximally.

17. A suturing device as in claim 16, wherein the shaft is slidably received in an axial lumen of the guide body.

18. A suturing device as in claim 12, wherein the needles each have arcuate ends near the tips.

19. A suturing device comprising:
a flexible shaft having a proximal end and a distal end;
a pair of needles removably carried near the distal end of the shaft, wherein each needle includes a shank carried near the distal end of the shaft and a sharpened tip disposed toward the proximal end of the shaft;
a length of suture extending between and secured near the tips of needles; and
a guide body having a proximal end, a distal end, means for slidably receiving the flexible shaft, means fixed near the distal end of the guide body for guiding the needles as the shaft is drawn proximally relative to the guide body, and means proximal of the guiding means on the guide body for receiving the needles and passing the needles to the proximal end of the guide body as the shaft is drawn proximally relative to the guide body;
whereby the flexible shaft may be introduced through a tissue tract and puncture site, advanced so that the sharpened needle tips pass beyond said puncture site, and the shaft then drawn proximally relative to the guide body so that the needles pass proximally through the tissue on either side of the puncture site.

20. A suturing device as in claim 19, wherein the guide body is a tubular structure having a central lumen which receives the flexible shaft and wherein the needle receiving means comprises two transversely offset axial lumens for receiving the pair of needles, respectively.

21. A suturing device as in claim 20, wherein the tubular structure has an additional lumen which permits the detection of blood when the distal end of the guide body enters a blood vessel.

22. A suturing device as in claim 20, further comprising a flexible sheath attached to and extending distally from the distal end of the guide body, wherein said sheath receives the shaft and needles prior to the shaft being drawn proximally and the needles drawn into the guide body.

23. A suturing device as in claim 22, wherein the flexible sheath includes at least one axial side lumen for receiving suture.

24. A suturing device as in claim 20, wherein the guide body has a guide tip at its distal end, wherein the guide tip includes channels which receive the distal ends of the needles and which direct the needles toward the transversely offset lumens as the shaft is drawn proximally.

25. A suturing device as in claim 19, wherein the needles are carried in a support holster near the distal end of the shaft, and wherein the support holster extends distally of the distal end of the guide body by at least 5 cm prior to the shaft being drawn proximally.

26. A suturing device as in claim 19, wherein the guide body is a tubular structure having a central lumen which receives the flexible shaft and two transversely offset axial lumens for receiving the pair of needles, respectively.

27. A suturing device as in claim 26, further comprising a flexible sheath attached to and extending distally from the distal end of the guide body, wherein said sheath receives the shaft and needles prior to the shaft being drawn proximally and the needles drawn into the guide body.

28. A suturing device as in claim 27, wherein the flexible sheath includes at least one axial side lumen for receiving suture.

29. A suturing device as in claim 26, wherein the guide body has a guide tip at its distal end, wherein the guide tip includes channels which receive the distal ends of the needles and which direct the needles toward the transversely offset lumens as the shaft is drawn proximally.

30. A suturing device as in claim 19, wherein the needles are carried in a support holster near the distal end of the shaft, and wherein the support holster extends distally of the distal end of the guide body by at least 5 cm prior to the shaft being drawn proximally.

31. A suturing device comprising:
a flexible shaft having a proximal end and a distal end;
a pair of needles removably carried near the distal end of the shaft, wherein each needle includes a shank carried near the distal end of the shaft and a sharpened tip disposed toward the proximal end of the shaft;
a length of suture extending between and secured near the tips of needles;
a guide body having a proximal end, a distal end, means for slidably receiving the flexible shaft, and means for guiding the needles as the shaft is drawn proximally relative to the guide body; and
a flexible sheath attached to and extending distally from the distal end of the guide body, wherein said sheath receives the shaft and needles prior to the shaft being drawn proximally and the needles drawn into the guide body;
whereby the flexible shaft may be introduced through a tissue tract and puncture site, advanced so that the sharpened needle tips pass beyond said puncture site, and the shaft then drawn proximally relative to the guide body so that the needles pass proximally through the tissue on either side of the puncture site.

32. A suturing device as in claim 31, wherein the guide body is a tubular structure having a central lumen which receives the flexible shaft and two transversely offset axial lumens for receiving the pair of needles, respectively.

33. A suturing device as in claim 32, wherein the tubular structure has an additional lumen which permits the detection of blood when the distal end of the guide body enters a blood vessel.

34. A suturing device as in claim 31, wherein the flexible sheath includes at lest one axial side lumen for receiving suture.

35. A suturing device as in claim 31, wherein the guide body has a guide tip at its distal end, wherein the guide tip includes channels which receive the distal ends of the needles and which direct the needles toward the transversely offset lumens as the shaft is drawn proximally.

36. A suturing device as in claim 31, wherein the needles are carried in a support holster near the distal end of the shaft, and wherein the support holster extends distally of the distal end of the guide body by at least 5 cm prior to the shaft being drawn proximally.

37. A suturing device comprising:
a flexible shaft having a proximal end, a distal end, and two transversely offset axial lumens;
a pair of needles removably carried near the distal end of the shaft, wherein each needle includes a shank carried near the distal end of the shaft and a sharpened tip disposed toward the proximal end of the shaft;
a length of suture extending between and secured near the tips of needles; and
a guide body having a proximal end, a distal end, means for slidably receiving the flexible shaft, means for guiding the needles as the shaft is drawn proximally relative to the guide body, and a guide tip at its distal end, wherein the guide tip includes channels which receive the distal ends of the needles and which direct the needles toward the transversely offset lumens as the shaft is drawn proximally;
whereby the flexible shaft may be introduced through a tissue tract and puncture site, advanced so that the sharpened needle tips pass beyond said puncture site, and the shaft then drawn proximally relative to the guide body so that the needles pass proximally through the tissue on either side of the puncture site.

38. A suturing device as in claim 37, wherein the guide body is a tubular structure having a central lumen between the two transversely offset axial lumens.

39. A suturing device as in claim 38, wherein the tubular structure has an additional lumen which permits the detection of blood when the distal end of the guide body enters a blood vessel.

40. A suturing device as in claim 37, further comprising a flexible sheath attached to and extending distally from the distal end of the guide body, wherein said sheath receives the shaft and needles prior to the shaft being drawn proximally and the needles drawn into the guide body.

41. A suturing device as in claim 40, wherein the flexible sheath includes at least one axial side lumen for receiving suture.

42. A suturing device as in claim 37, wherein the needles are carried in a support holster near the distal end of the shaft, and wherein the support holster extends distally of the distal end of the guide body by at least 5 cm prior to the shaft being drawn proximally.

43. A suturing device comprising:
a flexible shaft having a proximal end and a distal end;
a pair of needles removably carried near the distal end of the shaft, wherein each needle includes a shank carried near the distal end of the shaft and a sharpened tip disposed toward the proximal end of the shaft;
a length of suture extending between and secured near the tips of needles; and
a guide body having a proximal end, a distal end, means for slidably receiving the flexible shaft, means for guiding the needles as the shaft is drawn proximally relative to the guide body and a lumen which permits the detection of blood when the distal end of the guide body enters a blood vessel;
whereby the flexible shaft may be introduced through a tissue tract and puncture site, advanced so that the sharpened needle tips pass beyond said puncture site, and the shaft then drawn proximally relative to the guide body so that the needles pass proximally through the tissue on either side of the puncture site.

* * * * *